United States Patent [19]

Aulbach et al.

[11] Patent Number: 5,565,534
[45] Date of Patent: Oct. 15, 1996

[54] PROCESS FOR THE PREPARATION OF POLYOLEFINS

[75] Inventors: Michael Aulbach, Hofheim; Bernd Bachmann, Eppstein; Gerhard Erker; Christian Psiorz, both of Münster; Frank Küber, Oberursel; Frank Osan, Kelkheim; Thomas Weller, Mainz; Hans-Friedrich Herrmann, Darmstadt, all of Germany

[73] Assignee: Hoechst AG, Germany

[21] Appl. No.: 360,609

[22] Filed: Dec. 21, 1994

[30] Foreign Application Priority Data

Dec. 21, 1993 [DE] Germany ........................ 43 43 566.1
Sep. 14, 1994 [DE] Germany ........................ 44 32 617.3
Oct. 10, 1994 [DE] Germany ........................ 44 36 106.8

[51] Int. Cl.$^6$ .................................................. C08F 4/642
[52] U.S. Cl. ...................... 526/160; 526/126; 526/127; 526/170; 526/351; 526/352; 526/282; 526/943
[58] Field of Search ................................ 526/126, 127, 526/160, 170

[56] References Cited

U.S. PATENT DOCUMENTS

| | | | |
|---|---|---|---|
| 5,008,228 | 4/1991 | Chang | 502/111 |
| 5,122,583 | 6/1992 | Ewen et al. | 526/125 |
| 5,308,811 | 5/1994 | Suga et al. | 502/62 |
| 5,442,020 | 8/1995 | Davis | 526/160 |
| 5,491,205 | 2/1996 | Langhauser et al. | 526/121 |

FOREIGN PATENT DOCUMENTS

| | | |
|---|---|---|
| 0528041 | 2/1993 | European Pat. Off. . |
| 0650981 | 3/1995 | European Pat. Off. . |
| 0650973 | 5/1995 | European Pat. Off. . |
| WO93/20113 | 10/1993 | WIPO . |

*Primary Examiner*—Mark Nagumo
*Attorney, Agent, or Firm*—Connolly & Hutz

[57] ABSTRACT

The present invention relates to a process for the preparation of a polyolefin by polymerization of at least one olefin in the presence of a stereorigid metallocene compound containing, as ligands, at least two substituted or unsubstituted cyclopentadienyl groups bonded to one another via a monocyclic or polycyclic ring system, in which at least one cyclopentadienyl group is fused to the monocyclic or polycyclic ring system.

10 Claims, No Drawings

PROCESS FOR THE PREPARATION OF POLYOLEFINS

The present invention relates to a process for the preparation of polyolefins in the presence of a specific stereorigid metallocene compound.

The literature discloses the preparation of polyolefins by means of soluble metallocene compounds in combination with aluminoxanes or other cocatalysts which, due to their Lewis acidity, are able to convert the neutral metallocene into a cation and stabilize it (El 129 368, EP 351 392).

The published proceedings of the 1st Journal of Organometallic Chemistry Conference on Applied Organometallic Chemistry, page 136, describe metallocenes which contain a substituted tricyclic hydrocarbon as ligand system.

Use of soluble metallocene compounds based on bis(cyclopentadienyl)dialkylzirconium or his (cyclopentadienyl)-zirconium dihalide in combination with oligomeric aluminoxanes gives atactic polymers which, due to their unbalanced and inadequate product properties, are only of low industrial significance. In addition, certain olefin copolymers are not accessible.

Derivatives of zirconocene dichloride in which the two substituted cyclopentadienyl groups are bonded to one another via a methyl, ethylene or dimethylsilyene bridge can, due to their conformative rigidity, be used as catalysts for the isospecific polymerization of olefins (Chem. Lett. 1989, pp 1853–1856, or EP-A 0 316 155). Metallocenes containing (substituted) indenyl radicals as ligands are particularly important for the preparation of highly isotactic polymers of high crystallinity and high melting point (EP 485 823, EP 530 647).

Of considerable interest, however, are products whose property profile is between these two extremes and certain olefin copolymers.

The object was to provide a catalyst system which avoids the disadvantages of the prior art and is suitable for the preparation of certain olefin homopolymers and olefin copolymers, in particular polyolefins of reduced crystallinity, increased impact strength, increased transparency, high flowability at the processing temperature, low molecular weight and reduced melting point.

The present invention thus relates to a process for the preparation of a polyolefin by polymerization of at least one olefin in the presence of a stereorigid metallocene compound which contains, as ligands, at least two substituted or unsubstituted cyclopentadienyl groups which are bonded to one another via a monocyclic or polycyclic ring system wherein at least one cyclopentadienyl group is fused to the monocyclic or polycyclic ring system.

When determining the number of ring atoms in the monocyclic or polycyclic ring system, the carbon atoms of the cyclopentadienyl group(s) fused to the ring system which, due to the fusing, are parts of the ring system are also counted. Substituents on the monocyclic or polycyclic ring system are not counted.

In a preferred embodiment, one cyclopentadienyl group is a substitutent on the monocyclic or polycyclic ring system (ie. the cyclopentadienyl group is bonded to the ring system via a covalent bond), while a further cyclopentadienyl group is fused to the monocyclic or polycyclic ring system.

The monocyclic or polycyclic ring system may be aromatic, aliphatic or mixed aromatic and aliphatic and may also contain heteroatoms, such as nitrogen, oxygen, sulfur, silicon or germanium. It preferably contains 6–40, particularly preferably 6–20, ring atoms, in particular carbon ring atoms. The monocyclic or polycyclic ring system may also carry substituents, such as a $C_1$–$C_{40}$-hydrocarbon-containing group.

Fused cyclopentadienyl groups are monofused (for example via the 1,2- or 1,3-position of the cyclopentadienyl ring) or polyfused (for example via the 1,2,3- or 1,2,3,4-position of the cyclopentadienyl ring), preferably monofused, to the mono- or polycyclic ring system.

The central unit $M^1R^x_n$ of the metallocene compound according to the invention preferably comprises a transition-metal atom $M^1$, in particular from group IIIb, IVb, Vb or VIb of the Periodic Table of the Elements, which carries n substituents $R^x$, which are identical or different and are preferably a $C_1$–$C_{40}$-hydrocarbon-containing group, a halogen atom, an OH group or a hydrogen atom. The total of the number of substituents $R^x$ and the number of substituted or unsubstituted cyclopentadienyl groups (ligands) corresponds to the valency of the transition-metal atom $M^1$.

Preference is given in the process according to the invention to stereorigid metellocene compounds containing a ligand system which is different from 4-($\eta^5$-3'-alkyl-cyclopentadienyl)-4,6,6-trimethyl($\eta^5$-2-alkyl-4,5-tetra-hydropentalene).

Particular preference is given to compounds of the formula I

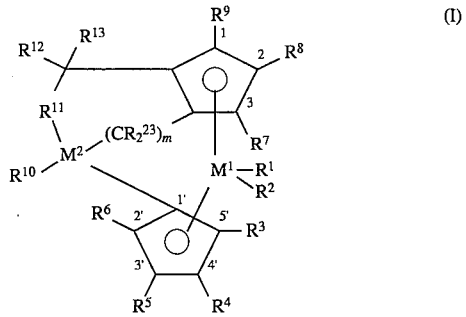

in which
$M^1$ is a metal from group IIIb, IVb, Vb or VIb of the Periodic Table,
$M^2$ is carbon, silicon, or germanium,
$R^1$ and $R^2$ are identical or different and are a hydrogen atom, a $C_1$–$C_{40}$-hydrocarbon-containing group, such as a $C_1$–$C_{10}$-alkyl group, a $C_1$–$C_{10}$-alkoxy group, a $C_6$–$C_{10}$-aryl group, a $C_6$–$C_{25}$-aryloxy group, a $C_2$–$C_{10}$-alkenyl group, a $C_7$–$C_{40}$-arylalkyl group or a $C_7$–$C_{40}$-arylalkenyl group, an OH group, a halogen atom or $NR^{14}_2$, in which $R^{14}$ is a halogen atom, a $C_1$–$C_{10}$-alkyl group or a $C_6$–$C_{10}$-aryl group, or $R^1$ and $R^2$ together with the atoms connecting them, from a ring system,
$R^3$, $R^4$, $R^5$, $R^6$, $R^7$, $R^8$, and $R^9$ are identical or different and are a hydrogen atom, a halogen atom, a $C_1$–$C_{20}$-hydrocarbon-containing group, such as a $C_1$–$C_{10}$-alkyl group, which may be halogenated, a $C_6$–$C_{20}$-aryl group, a $C_6C_{20}$-aryloxy group, a $C_2$–$C_{12}$-alkenyl group, a $C_7$–$C_{40}$-arylalkyl group, a $C_7$–$C_{40}$-alkylaryl group or a $C_8$–$C_{40}$-arylalkenyl group, a —$SiR^{14}_3$, $NR^{14}_2$, —$SiOR^{14}_3$, —$SiSR^{14}_3$, or —$PR^{14}_2$, radical, in which $R^{14}$ is a halogen atom, a $C_1$–$C_{10}$-alkyl group or a $C_6$–$C_{10}$-aryl group or two or more adjacent radicals $R^3$, $R^4$, $R^5$, $R^6$, $R^7$, $R^8$, and $R^9$, together with the atoms connecting them, form a ring system preferably containing 4–40, particularly preferably 6–15, carbon atoms,
$R^{10}$ is a hydrogen atom, a $C_1$–$C_{40}$-hydrocarbon-containing group, such as a $C_1$–$C_{20}$ alkyl group, a $C_1$–$C_{10}$-alkoxy group, a $C_6$–$C_{20}$-aryl group, a $C_6$–$C_{20}$-aryloxy group, a $C_2$–$C_{12}$-alkenyl group, a $C_7$–$C_{40}$-arylalkyl group, a $C_7$–$C_{40}$-alkylaryl group or a $C_8$–$C_{40}$-arylalkenyl group, each of which may carry —$NR^{14}_3$, —$SiR^{14}_3$, —$SR^{14}_2$ or —OSiR$^{14}_3$ radicals, in which R$^{14}$ is a halogen atom, a C$_1$–C$_{10}$-alkyl group or a C$_6$–C$_{10}$-aryl group, or R$^{10}$ is connected to one or more of the radicals R$^3$, R$^4$, R$^5$ and R$^6$, R$^{11}$ is

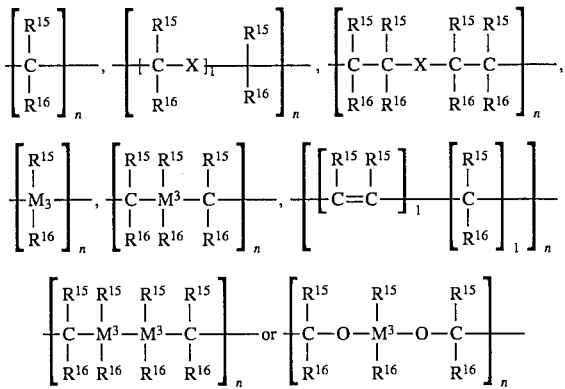

where n is an integer from 1 to 20, l is an integer from 0 to 20, X is O, =NR$^{14}$, =CO, =PR$^{14}$, =P(O)R$^{14}$=SO, =SO$_2$ or —S—, in which R$^{14}$ is a halogen atom, a C$_1$–C$_{10}$-alkyl group or a C$_6$–C$_{10}$-aryl group.

R$^{15}$ and R$^{16}$ are identical or different and are a hydrogen atom, a halogen atom or a C$_1$–C$_{40}$-hydrocarbon-containing group, such as a C$_1$–C$_{10}$-alkyl group, a C$_1$–C$_{10}$-fluoroalkyl group, a C$_1$–C$_{10}$-alkoxy group, a C$_6$–C$_{10}$-aryl group, a C$_6$–C$_{10}$-fluoroaryl group, a C$_6$–C$_{10}$-aryloxy group, a C$_2$–C$_{10}$-alkenyl group, a C$_7$–C$_{40}$-arylalkyl group, a C$_7$–C$_{40}$-alkylaryl group, or a C$_8$–C$_{40}$-arylalkenyl group or two radicals R$^{15}$, two radicals R$^{16}$ or R$^{15}$ and R$^{16}$, in each case together with the atoms connecting them, form one or more rings, and M$^3$ is silicon, germanium or tin, R$^{12}$ and R$^{13}$ are identical or different and are a hydrogen atom, a C$_1$–C$_{40}$-hydrocarbon-containing group, such as a C$_1$–C$_{20}$-alkyl group, a C$_1$–C$_{10}$-alkoxy group, a C$_6$–C$_{20}$-aryl group, a C$_6$–C$_{20}$-aryloxy group, a C$_2$–C$_{12}$-alkenyl group, a C$_7$–C$_{40}$-arylalkyl group, a C$_7$–C$_{40}$-alkylaryl group or a C$_8$–C$_{40}$-arylalkenyl group, each of which may carry —NR$^{14}_3$ is a —SR$^{14}_2$, —SiR$^{14}_3$ or —OSiR$^{14}_3$ radicals, in which R$^{14}$ is a halogen atom, a C$_1$–C$_{10}$-alkyl group or a C$_6$–C$_{10}$-aryl group, or may carry halogen, R$^{23}$ is identical or different and is a hydrogen atom, a halogen atom or a C$_1$–C$_{40}$-hydrocarbon-containing group, such as a C$_1$–C$_{10}$-alkyl group, a C$_1$–C$_{10}$-alkoxy group, a C$_6$–C$_{10}$-aryl group, a C$_6$C$_{25}$-aryoxy group, a C$_2$–C$_{10}$-alkenyl group, a C$_7$–C$_{40}$-arylalkyl group or a C$_7$–C$_{40}$-arylalkenyl group, or one or more radicals R$^{23}$ are bonded to one or both radicals R$^{15}$ and R$^{16}$ and/or to one or more radicals R$^{10}$, R$^{11}$, R$^{12}$ and R$^{13}$, and m is an integer from 0 to 24.

In the case where M$^2$ is C, m is 0 and R$^{11}$ is CH$_2$, preferably at least one of the radicals R$^4$, R$^8$, R$^{10}$, R$^{12}$ and R$^{13}$ is not alkyl and/or at least one of the radicals R$^3$, R$^5$, R$^6$, R$^7$ and R$^9$ is not hydrogen.

For compounds of the formula I, it is preferred that M$^1$ is zirconium or hafnium, in particular zirconium, R$^1$ and R$^2$ are identical and are a C$_1$–C$_3$-alkyl group or a halogen atom, in particular chlorine, R$^3$, R$^4$, R$^5$, R$^6$, R$^7$, R$^8$ and R$^9$ are identical or different and are a hydrogen atom, a C$_1$–C$_{10}$-alkyl group or a C$_6$–C$_{24}$-aryl group, or two or more adjacent radicals, together with the atoms connecting them, form an aromatic or aliphatic hydrocarbon ring system, R$^{10}$ is a hydrogen atom, a C$_6$–C$_{24}$-aryl group or a C$_1$–C$_{10}$-alkyl group, in particular a C$_1$–C$_4$-alkyl group, R$^{11}$ is

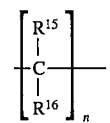

wherein n is an integer from 1 to 8, in particular from 2 to 4,

R$^{15}$ and R$^{16}$ are identical or different and are hydrogen or a C$_1$–C$_{10}$-alkyl group, or two radicals R$^{15}$, two radicals R$^{16}$ or R$^{15}$ and R$^{16}$, together with the atoms connecting them, form a hydrocarbon ring system, M$^2$ is carbon, R$^{12}$ and R$^{13}$ are identical or different and are a hydrogen atom, a C$_1$–C$_{10}$-alkyl group, in particular a C$_1$–C$_4$-alkyl group, or a C$_6$–C$_{10}$-aryl group, and m is 0.

Particular preference is given to compounds of the formula I in which

M$^1$ is zirconium,

R$^1$ and R$^2$ are identical and are a halogen atom, in particular chlorine,

R$^3$, R$^4$, R$^5$, R$^6$, R$^7$, R$^8$ and R$^9$ are identical or different and are hydrogen or a C$_1$–C$_4$-alkyl group, such as methyl, ethyl, propyl, isopropyl butyl or isobutyl, or a C$_6$–C$_{14}$-aryl group, such as phenyl or naphthyl or R$_8$ and R$_9$ and R$_3$ and R$_4$ and/or R$_5$ and R$_6$, together with the atoms connecting them, form an aromatic hydrocarbon ring system, in particular a six-membered ring, which may itself be substituted, M$^2$ is a carbon atom, R$^{10}$ is a C$_1$–C$_6$-alkyl group in particular methyl, R$^{11}$ is —CH$_2$—CH$_2$—, R$^2$ and R$^{13}$ are identical or different and are a methyl or phenyl group, and m is 0.

Preferably, at least one of the radicals R$^3$ to R$^9$, in particular at least one of the radicals R$_4$, R$^5$ and R$^8$, is other than hydrogen, in particular if R$^{11}$ is —CH$_2$—CH$_2$—.

Examples of metallocene compounds according to the invention are:

[4-($\eta^5$-cyclopentadienyl)-4,7,7-trimethyl($\eta^5$-4,5,6,7-tetrahydroindenyl)]dichlorotitanium,

[4-($\eta^5$-cyclopentadienyl)-4,7,7-trimethyl($\eta^5$-4,5,6,7-tetrahydroindenyl)]dichlorozirconium,

[4-($\eta^5$-cyclopentadienyl)-4,7,7-trimethyl($\eta^5$-4,5,6,7-tetrahydroindenyl)]dichlorohafnium,

[4-($\eta^5$-cyclopentadienyl)-4,7,7-triphenyl($\eta^5$-4,5,6,7-tetrahydroindenyl)]dichlorotitanium,

[4-($\eta^5$-cyclopentadienyl)-4,7,7-triphenyl($\eta^5$-4,5,6,7-tetrahydroindenyl)]dichlorozirconium,

[4-($\eta^5$-cyclopentadienyl)-4,7-dimethyl-7-phenyl($\eta^5$-4,5,6,7-tetrahydroindenyl)]dichlorotitanium,

[4-($\eta^5$-cyclopentadienyl)-4,7-dimethyl-7-phenyl($\eta^5$-4,5,6,7-tetrahydroindenyl)]dichlorozirconium,

[4-($\eta^5$-cyclopentadienyl)-4,7-dimethyl-7-naphthyl($\eta^5$-4,5,6,7-tetrahydroindenyl)]dichlorotitanium,

[4-($\eta^5$-cyclopentadienyl)-4,7-dimethyl-7-naphthyl($\eta^5$-4,5,6,7-tetrahydroindenyl)]dichlorozirconium,

[4-($\eta^5$-cyclopentadienyl)-4,7-dimethyl-7-butyl($\eta^5$-4,5,6,7-tetrahydroindenyl)]dichlorotitanium,

[($\eta^5$-cyclopentadienyl)-4,7-dimethyl-7-butyl($\eta^5$-4,5,6,7-tetrahydrahydroindenyl)dichlorozirconium,

[4-($\eta^5$-3'-tert-butylcyclopentadienyl)-4,7,7-trimethyl($\eta^5$-4,5,6,7-tetrahydroindenyl)]dichlorotitanium,

[4-($\eta^5$-3'-tert-butylcyclopentadienyl)-4,7,7-trimethyl($\eta^5$-4,5,6,7-tetrahydroindenyl)]dichlorozirconium,

[4-($\eta^5$-3'-tert-butylcyclopentadienyl)-4,7,7-triphenyl($\eta^5$-4,5,6,7-tetrahydroindenyl)]dichlorotitanium,

[4-($\eta^5$-3'-tert-butylcyclopentadienyl)-4,7,7-triphenyl($\eta^5$-4,5,6,7-tetrahydroindenyl)]dichlorozirconium,
[4-($\eta^5$-3'-tert-butylcyclopentadienyl)-4,7-dimethyl-7-phenyl($\eta^5$-4,5,6,7-tetrahydroindenyl)]dichlorotitanium,
[4-($\eta^5$-3'-tert-butylcyclopentadienyl)-4,7-dimethyl-7-phenyl($\eta^5$-4,5,6,7-tetrahydroindenyl)]dichlorozirconium,
[4-($\eta^5$-3'-tert-butylcyclopentadienyl)-4,7-dimethyl-7-naphthyl($\eta^5$- 4,5,6,7-tetrahydroindyl)]dichlorotitanium,
[4-($\eta^5$-3'-tert-butylcyclopentadienyl)-4,7-dimethyl-7-naphthyl($\eta^5$-4,5,6,7-tetrahydroindenyl)]dichlorozirconium,
[4-($\eta^5$-3'-tert-butylcyclopentadienyl)-4,7-dimethyl-7-butyl($\eta^5$-4,5,6,7-tetrahydroindenyl)]dichlorotitanium,
[4-($\eta^5$-3'-tert-butylcyclopentadienyl)-4,7-dimethyl-7-butyl($\eta^5$-4,5,6,7-tetrahydroindenyl)]dichlorozirconium,
[4-($\eta^5$-indenyl)-4,7,7-trimethyl($\eta^5$-4,5,6,7-tetrahydroindenyl)]dichlorotitanium,
[4-($\eta^5$-3'-indenyl)-4,7,7-trimethyl($\eta^5$-4,5,6,7-tetrahyroindenyl)]dichlorozirconium,
[4-($\eta^5$-indenyl)-4,7,7-triphenyl($\eta^5$-4,5,6,7-tetrahydroindenyl)]dichlorotitanium,
[4-($\eta^5$-indenyl)-4,7,7-triphenyl($\eta^5$-4,5,6,7-tetrahydroindenyl)]dichlorozirconium,
[4-($\eta^5$-indenyl)-4,7-dimethyl-7-phenyl($\eta^5$-4,5,6,7-tetrahydroindenyl)]dichlorotitanium,
[4-($\eta^5$-indenyl)-4,7-dimethyl-7-phenyl($\eta^5$-4,5,6,7-tetrahydroindenyl)]dichlorozirconium,
[4-($\eta^5$-indenyl)-4,7-dimethyl-7-phenyl($\eta^5$-4,5,6,7-tetrahydroindenyl)]dichlorotitanium,
[4-($\eta^5$-indenyl)-4,7-dimethyl-7-phenyl($\eta^5$-4,5,6,7-tetrahydroindenyl)]dichlorozirconium,
[4-($\eta^5$-indenyl)-4,7-dimethyl-7-butyl($\eta^5$-4,5,6,7-tetrahydroindenyl)]dichlorotitanium,
[4-($\eta^5$-indenyl)-4,7-dimethyl-7-butyl($\eta^5$-4,5,6,7-tetrahydroindenyl)]dichlorozirconium,
[4-($\eta^5$-cyclopentadienyl)-4,7,7-trimethyl($\eta^5$-4,5,6,7-tetrahydrofluorenyl)]dichlorotitanium,
[4-($\eta^5$-cyclopentadienyl)-4.7,7-trimethyl($\eta^5$-4,5,6,7-tetrahydrofluorenyl)]dichlorozirconium,
[4-($\eta^5$-cyclopentadienyl)-4,7,7-triphenyl($\eta^5$-4,5,6,7-tetrahydrofluorenyl)]dichlorotitanium,
[4-($\eta^5$-cyclopentadienyl)-4,7,7-triphenyl($\eta^5$-4,5,6,7-tetrahdrofluorenyl)]dichlorozirconium,
[4-($\eta^5$-cyclopentadienyl)-4,7-dimethyl-7-phenyl ($\eta^5$-4,5,6,7-tetrahydrofluorenyl)]dichlorotitanium,
[4-($\eta^5$-cyclopentadienyl)-4,7-dimethyl-7-phenyl($\eta^5$-4,5,6,7-tatrahydrofluorenyl)]dichlorozirconium,
[4-($\eta^5$cyclopentadienyl)-4,7-dimethyl-7-naphthyl($\eta^5$-4,5,6,7-tetrahydrafluorenyl)]dichlorotitanium,
[4-($\eta^5$-cyclopentadienyl)-4,7-dimethyl-7-naphthyl-($\eta^5$-4,5,6,7-tetrahydrofluarenyl)]dichlorozirconium,
[4-($\eta^5$-cyclopentadienyl)-4,7-dimethyl-7-butyl($\eta^5$-4,5,6,7-tetrahydrofluorenyl)]dichlorotitanium,
[4-($\eta^5$-cyclopentadienyl)-4,7-dimethyl-7-butyl($\eta^5$-4,5,6,7-tetrahydrofluorenyl)]dichlorozirconium,
[4-($\eta^5$-3'-methylcyclopentadienyl)-4,7,7-trimethyl-($\eta^5$-4,5,6,7,-tetrahydroindenyl)]dichlorotitanium,
[4-($\eta^5$-3'-methylcyclopentadienyl)-4,7,7-trimethyl-($\eta^5$-4,5,6,7-tetrahydroindenyl)]dichlorozirconium,
[4-($\eta^5$-3'-methylcyclopentadienyl)-4,7,7-triphenyl-($\eta^5$-4,5,6,7,-tetrahydroindenyl)]dichlorotitanium,
[4-($\eta^5$-3'-methylcyclopentadienyl) -4,7,7-triphenyl-($\eta^5$-4,5,6,7-tetrahydroindenyl)]dichlorozirconium,
[4-($\eta^5$-3'-methylcyclopentadienyl)-4,7-dimethyl-7-phenyl-($\eta^5$-4,5,6,7-tetrahydroindenyl)]dichlorotitanium,
[4-($\eta^5$-3'-methylcyclopantadienyl)-4,7-dimethyl-7-phenyl-($\eta^5$-4,5,6,7-tetrahydroindenyl)]dichlorozirconium,
[4-($\eta^5$-3'-methylcyclopentadienyl)-4,7-dimethyl-7-naphthyl($\eta^5$-4,5,6,7-tetrahydroindenyl)]dichlorotitanium,
[4-($\eta^5$-3'-methylcyclopentadienyl)-4,7-dimethyl-7-naphthyl($\eta^5$-4,5,6,7-tetrahydroindenyl)]dichlorozirconium,
[4-($\eta^5$-3'-methylcyclopentadienyl)-4,7-dimethyl-7-butyl($\eta^5$- 4,5,6,7-tetrahydroindenyl)]dichlorotitanium,
[4-($\eta^5$-3'-methycyclopentadienyl)-4,7-dimethyl-7-butyl ($\eta^5$-4,5,6,7-tetrahydroindenyl)]dichlorozirconium,
[4-($\eta^5$-cyclopentadienyl)-4,7,7-trimethyl($\eta^5$-2-methyl-4,5,6,7-tetrahydroindenyl)]dichlorotitanium,
[4-($\eta^5$-cyclopentadienyl)-4,7,7-trimethyl($\eta^5$-2-methyl-4,5,6,7-tetrahydroindenyl)]dichlorozirconium,
[4-($\eta^5$-cyclopentadienyl)-4,7,7-triphenyl($\eta^5$-2-methyl- 4,5,6,7-tetrahydroindenyl)]dichlorotitanium,
[4-($\eta^5$-cyclopentadienyl)-4,7,7-triphenyl($\eta^5$-2-methyl-4,5,6,7-tetrahydroindenyl)]dichlorozirconium,
[4-($\eta^5$-cyclopentadienyl)-4,7-dimethyl-7-phenyl($\eta^5$-2-methyl-4,5,6,7-tetrahydroindenyl)]dichlorotitanium,
[4-($\eta^5$-cyclopentadienyl)-4,7-dimethyl-7-phenyl ($\eta^5$-2-methyl-4,5,6,7-tetrahydroindenyl)]dichlorozirconium,
[4-($\eta^5$-cyclopentadienyl)-4,7-dimethyl-7-naphthyl($\eta^5$-2-methyl-4,5,6,7-tetrahydroindenyl)]dichlorotitanium,
(4-($\eta^5$-cyclopentadienyl)-4,7-dimethyl-7-naphthyl($\eta^5$-2-methyl-4,5,6,7-tetrahydroindenyl)]dichlorozirconium,
[4-$\eta^5$-cyclopentadienyl)-4,7-dimethyl-7-butyl($\eta^5$-2-methyl-4,5,6,7-tetrahydroindenyl)]dichlorotitanium,
[4-($\eta^5$-cyclopentadienyl)-4,7-dimethyl-7-butyl($\eta^5$-2-methyl-4,5,6,7-tetrahydroindenyl)]dichlorozirconium,
[4-($\eta^5$-3'-methylcyclopentadienyl)-4,7,7-trimethyl($\eta^5$-2-methyl-4,5,6,7-tetrahydroindenyl)]dichlorotitanium,
[4-($\eta^5$-3'-methylcyclopentadienyl)-4,7,7-trimethyl($\eta^5$-2-methyl-4,5,6,7-tetrahydroindenyl)]dichlorozirconium,
[4-($\eta^5$-3'-methylcyclopentadienyl)-4,7,7-triphenyl($\eta^5$-2-methyl-4,5,6,7-tetrahydroindenyl)]dichlorotitanium,
[4-($\eta^5$-3'-methylcyclopentadienyl)-4,7,7-triphenyl($\eta^5$-2-methyl-4,5,6,7-tetrahydroindenyl)]dichlorozirconium,
[4-($\eta^5$-3'-methylcyclopentadienyl)-4,7-dimethyl-7-phenyl($\eta^5$-2-methyl-4,5,6,7-tetrahydroindenyl)]-dichlorotitanium,
[4-($\eta^5$-3'-methylcyclopentadienyl)-4,7-dimethyl-7-phenyl($\eta^5$-3'-methyl-4,5,6,7-tetrahydroindenyl)]-dichlorozirconium,
[4-($\eta^5$-3'-methylcyclopentadienyl)-4,7-dimethyl-7-naphthyl($\eta^5$-2-methyl-4,5,6,7-tetrahydroindenyl)]-dichlorotitanium,
[4-($\eta^5$-3'-methylcyclopentadienyl)-4,7-dimethyl-7-naphthyl($\eta^5$-2-methyl-4,5,6,7-tetrahydroindenyl)]-dichlorozirconium,
[4-($\eta^5$-3'-methylcyclopentadienyl)-4,7-dimethyl-7-butyl($\eta^5$-2-methyl-4,5,6,7-tetrahydroindenyl)]-dichlorotitanium,
[4-$\eta^5$-3'-methylcyclopentadienyl)-4,7-dimethyl-7-butyl($\eta^5$-2-methyl-4,5,6,7-tetrahydroindenyl)]dichlorozirconium,
[4-($\eta^5$-fluorenyl)-4,7,7-trimethyl($\eta^5$-4,5,6,7-tetrahydroindenyl)]dichlorotitanium,
[4-($\eta^5$-fluorenyl)-4,7,7-trimethyl($\eta^5$-4,5,6,7-tetrahydroindenyl)]dichlorozirconium,
[4-($\eta^5$-fluorenyl)-4,7,7-triphenyl($\eta^5$-4,5,6,7-tetrahydroindenyl)]dichlorotitanium,
[4-($\eta^5$-fluorenyl)-4,7,7-triphenyl($\eta^5$-4,5,6,7-tetrahydroindenyl)]dichlorozirconium,
[4-($\eta^5$-fluorenyl)-4,7-dimethyl-7-phenyl($\eta^5$-4,5,6,7-tetrahydroindenyl)]dichlorotitanium,
[4-($\eta^5$-fluorenyl)-4,7-dimethyl-7-phenyl($\eta^5$-4,5,6,7-tetrahydroindenyl)]dichlorozirconium,
[4-($\eta^5$-fluorenyl)-4,7-dimethyl-7-naphthyl($\eta^5$-4,5,6,7-tetrahydroindenyl)]dichlorotitanium,
[4-($\eta^5$-fluorenyl)-4,7-dimethyl-7-naphthyl($\eta^5$-4,5,6,7-tetrahydroindenyl)]dichlorozirconium,

[4-($\eta^5$-fluorenyl)-4,7-dimethyl-7-butyl($\eta^5$-4,5,6,7-tetrahydroindenyl)]dichlorotitanium,

[4-($\eta^5$-fluorenyl)-4,7-dimethyl-7-butyl($\eta^5$-4,5,6,7-tetrahydroindenyl)]dichlorozirconium,

[4-($\eta^5$-cyclopentadienyl)-4,7,7-trimethyl-4,5,6,7,10,11,12,13-octahydro-5,6-benzoindenyl]dichlorozirconium,

[5-($\eta^5$-cyclopentadienyl)-4,7,7-trimethyl($\eta^5$-4,5,6,7-tetrahydroindenyl)]dichlorotitanium,

[5-($\eta^5$-cyclopentadienyl)-4,7,7-trimethyl($\eta^5$-4,5,6,7-tetrahydroindenyl)]dichlorozirconium,

[5-($\eta^5$-cyclopentadienyl)-4,7,7-triphenyl($\eta^5$-4,5,6,7-tetrahydroindenyl)]dichlorotitanium,

[5-($\eta^5$-cyclopentadienyl)-4,7,7-triphenyl($\eta^5$-4,5,6,7-tetrahydroindenyl)]dichlorozirconium,

[5-($\eta^5$-cyclopentadienyl)-4,7-dimethyl-7-phenyl($\eta^5$-4,5,6,7-tetrahydroindenyl)]dichlorotitanium,

[5-($\eta^5$-cyclopentadienyl)-4,7-dimethyl-7-phenyl($\eta^5$-4,5,6,7-tetrahydroindenyl)]dichlorozirconium,

[5-($\eta^5$-cyclopentadienyl)-4,7-dimethyl-7-naphthyl($\eta^5$-4,5,6,7-tetrahydroindenyl)]dichlorotitanium,

[5-($\eta^5$-cyclopentadienyl)-4,7-dimethyl-7-naphthyl($\eta^5$-4,5,6,7-tetrahydroindenyl)]dichlorotitanium,

[5-($\eta^5$-cyclopentadienyl)-4,7-dimethyl-7-butyl($\eta^5$-4,5,6,7-tetrahydroindenyl)]dichlorotitanium,

[5-($\eta^5$-cyclopentadienyl)-4,7-dimethyl-7-butyl($\eta^5$-4,5,6,7-tetrahydroindenyl)]dichlorozirconium,

[5-($\eta^5$-3'-tert-butylcyclopentadienyl)-4,7,7-trimethyl($\eta^5$-4,5,6,7-tetrahydroindenyl)]dichlorotitanium,

[5-($\eta^5$-3'-tert-butylcyclopentadienyl)-4,7,7-trimethyl($\eta^5$-4,5,6,7-tetrahydroindenyl)]dichlorozirconium,

[5-($\eta^5$-3'-tert-butylcyclopentadienyl)-4,7,7-triphenyl($\eta^5$-4,5,6,7-tetrahydroindenyl)]dichlorotitanium,

[5-($\eta^5$-3'-tert-butylcyclopentadienyl)-4,7,7-triphenyl($\eta^5$-4,5,6,7-tetrahydroindenyl)]dichlorozirconium,

[5-($\eta^5$-3'-tert-butylcyclopentadienyl)-4,7-dimethyl-7-phenyl($\eta^5$-4,5,6,7-tetrahydroindenyl)]dichlorotitanium,

[5-($\eta^5$-3'-tert-butylcyclopentadienyl)-4,7-dimethyl-7-phenyl($\eta^5$-4,5,6,7-tetrahydroindenyl)]dichlorozirconium,

[5-($\eta^5$-3'-tert-butylcyclopentadienyl)-4,7-dimethyl-7-naphthyl($\eta^5$-4,5,6,7-tetrahydroindenyl)]dichlorotitanium,

[5-($\eta^5$-3'-tert-butylcyclopentadienyl)-4,7-dimethyl-7-naphthyl ($\eta^5$-4,5,6,7-tetrahydroindenyl)]dichlorozirconium,

[5-($\eta^5$-3'-tert-butylcyclopentadienyl)-4,7-dimethyl-7-butyl($\eta^5$-4,5,6,7-tetrahydroindenyl)]dichlorotitanium,

[5-($\eta^5$-3'-tert-butylcyclopentadienyl)-4,7-dimethyl-7-butyl ($\eta^5$-4,5,6,7-tetrahydroindenyl)]dichlorozirconium,

[5-($\eta^5$-indenyl)-4,7,7-trimethyl-($\eta^5$-4,5,6,7-tetrahydroindenyl)]dichlorotitanium,

[5-($\eta^5$-indenyl)-4,7,7-trimethyl-($\eta^5$-4,5,6,7-tetrahydroindenyl)]dichlorozirconium,

[5-($\eta^5$-indenyl)-4,7,7-triphenyl($\eta^5$-4,5,6,7-tetrahydroindenyl)]dichlorotitanium,

[5-($\eta^5$-indenyl)-4,7,7-triphenyl($\eta^5$-4,5,6,7-tetrahydroindenyl)]dichlorozirconium,

[5-($\eta^5$-indenyl)-4,7-dimethyl-7-phenyl($\eta^5$-4,5,6,7-tetrahydroindenyl)]dichlorotitanium,

[5-($\eta^5$-indenyl)-4,7-dimethyl-7-phenyl($\eta^5$-4,5,6,7-tetrahydroindenyl)]dichlorozirconium,

[5-($\eta^5$-indenyl)-4,7-dimethyl-7-naphthyl($\eta^5$-4,5,6,7-tetrahydroindenyl)]dichlorotitanium,

[5-($\eta^5$-indenyl)-4,7-dimethyl-7-naphthyl($\eta^5$-4,5,6,7-tetrahydroindenyl)]dichlorozirconium,

[5-($\eta^5$-indenyl)-4,7-dimethyl-7-butyl($\eta^5$-4,5,6,7-tetrahydroindenyl)]dichlorotitanium,

[5-($\eta^5$-indenyl)-4,7-dimethyl-7-butyl($\eta^5$-4,5,6,7-tetrahydroindenyl)]dichlorozirconium,

[5-($\eta^5$-cyclopentadienyl)-4,7,7-trimethyl($\eta^5$-4,5,6,7-tetrahydrofluorenyl)]dichlorotitanium,

[5-($\eta^5$-cyclopentadienyl)-4,7,7-trimethyl($\eta^5$-4,5,6,7-tetrahydrofluorenyl)]dichlorozirconium,

[5-($\eta^5$-cyclopentadienyl)-4,7,7-triphenyl($\eta^5$-4,5,6,7-tetrahydrofluorenyl)]dichlorotitanium,

[5-($\eta^5$-cyclopentadienyl)-4,7,7-triphenyl($\eta^5$-4,5,6,7-tetrahydrofluorenyl)]dichlorozirconium,

[5-($\eta^5$-cyclopentadienyl)-4,7-dimethyl-7-phenyl($\eta^5$-4,5,6,7-tetrahydrofluorenyl)]dichlorotitanium,

[5-($\eta^5$-cyclopentadienyl)-4,7-dimethyl-7-phenyl($\eta^5$-4,5,6,7-tetrahydrofluorenyl)]dichlorozirconium,

[5-($\eta^5$-cyclopentadienyl)-4,7-dimethyl-7-naphthyl($\eta^5$-4,5,6,7-tetrahydrafluorenyl)]dichlorotitanium,

[5-($\eta^5$-cyclopentadienyl)-4,7-dimethyl-7-naphthyl($\eta^5$-4,5,6,7-tetrahydrofluorenyl)]dichlorozirconium,

[5-($\eta^5$-cyclopentadienyl)-4,7-dimethyl-7-butyl($\eta^5$-4,5,6,7-tetrahydrofluorenyl)]dichlorotitanium,

[5-($\eta^5$-cyclopentadienyl)-4,7-dimethyl-7-butyl($\eta^5$-4,5,6,7-tetrahydrofluorenyl)]dichlorozirconium,

[5-($\eta^5$-fluorenyl)-4,7,7-trimethyl($\eta$-4,5,6,7-hydroindenyl)]dichlorotitanium,

[5-($\eta^5$-fluorenyl)-4,7,7-trimethyl($\eta^5$-4,5,6,7-tetrahydroindenyl)]dichlorozirconium,

[5-($\eta^5$-fluorenyl)-4,7,7-triphenyl($\eta^5$-4,5,6,7-tetrahydroindenyl)]dichlorotitanium,

[5-($\eta^5$-fluorenyl)-4,7,7-triphenyl($\eta^5$-4,5,6,7-tetrahydroindenyl)]dichlorozirconium,

[5-($\eta^5$-fluorenyl)-4,7-dimethyl-7-phenyl($\eta^5$-4,5,6,7-tetrahydroindenyl)]dichlorotitanium,

[5-($\eta^5$-fluorenyl)-4,7-dimethyl-7-phenyl($\eta^5$-4,5,6,7-tetrahydroindenyl)]dichlorozirconium,

[4-($\eta^5$-3'-isopropylcyclopentadienyl)-4,7,7-trimethyl-$\eta^5$-4,5,6,7-tetrahydroindenyl]dichlorozirconium

[4-($\eta^5$-4'-isopropylcyclopentadienyl)-4,7,7-trimethyl-$\eta^5$-4,5,6,7-tetrahydroindenyl]dichlorozirconium

[4-($\eta^5$-3'-isopropylcyclopentadienyl)-2-isopropyl-4,7,7-trimethyl-$\eta^5$-4,5,6,7-tetrahydroindenyl]dichlorozirconium

[4-($\eta^5$-4'-isopropylcyclopentadienyl)-2-isopropyl-4,7,7-trimethyl-$\eta^5$-4,5,5,7-tetrahydroindenyl]dichlorozirconium

[4-($\eta^5$-3'-isopropylcyclopentadienyl)-4,7-dimethyl-7-phenyl-$\eta^5$-4,5,6,7-tetrahydroindenyl]dichlorozirconium

[4-($\eta^5$-4'-isopropylcyclopentadienyl)-4,7-dimethyl-7-phenyl-$\eta^5$-4,5,6,7-tetrahydroindenyl]dichlorozirconium

[4-($\eta^5$-3'-isopropylcyclopentadienyl)-2-isopropyl-4,7-dimethyl-7-phenyl-$\eta^5$-4,5,6,7-tetrahydroindenyl]dichlorozirconium

[4-($\eta^5$-4'-isopropylcyclopentadienyl)-2-isopropyl-4,7-dimethyl-7-phenyl-$\eta^5$-4,5,6,7-tetrahydroindenyl]dichlorozirconium

[4-($\eta^5$-3'-trimethylsilylcyclopentadienyl)-4,7,7-trimethyl-$\eta^5$-4,5,6,7-tetrahydroindenyl]dichlorozirconium

[4-($\eta^5$-4'-trimethylsilylcyclopentadienyl)-4,7,7-trimethyl-$\eta^5$ -4,5,6,7-tetrahydroindenyl]dichlorozirconium

[4-($\eta^5$-3'-trimethylsilylcyclopentadienyl)-2-trimethylsilyl-4,7,7-trimethyl-$\eta^5$-4,5,6,7-tetrahydroindenyl]-dichlorozirconium

[4-($\eta^5$-4'-trimethylsilylcyclopentadienyl)-2-trimethylsilyl-4,7,7-trimethyl-$\eta^5$-4,5,6,7-tetrahydroindenyl]dichlorozirconium

[4-($\eta^5$-3'-(tert-butyldimethylsilyl)cyclopentadienyl-4,7,7-trimethyl-$\eta^5$-4,5,5,7-tetrahydroindenyl]dichlorozirconium

[4($\eta^5$-4'-(tert-butyldimethylsilyl)cyclopentadienyl)-4,7,7-trimethyl-$\eta^5$-4,5,6,7-tetrahydroindenyl]dichlorozirconium

[4-($\eta^5$-3'-(tert-butyldimethylsilyl)cyclopentadenyl-2-(tert-butyldimethylsilyl)-4,7,7-trimethyl-$\eta^5$-4,5,6,7-tetrahydroindenyl]dichlorozirconium

[4-(η⁵-4'-tert-butyldimethylsilyl)cyclopentadienyl)-2(tert-butyldimethylsilyl)- 4,7,7-trimethyl-(η⁵-4,5,6,7-tetrahydroindenyl]dichlorozirconium

[4-(η⁵-3'-(tert-butyldimethysilyl)cyclopentadienyl)-4,7-dimethyl-7-phenyl-η⁵-4,5,6,7-tetrahydroindenyl)dichlorozirconium

[4-(η⁵-4'-trimethylsilylcyclopentadienyl)-4,7-dimethyl-7-phenyl-η⁵-4,5,6,7-tetrahydroindenyl]dichlorozirconium

[4-(η⁵-3'-trimethylsilylcyclopentadienyl)-2-trimethylsilyl-4,7-dimethyl-7-phenyl-η⁵-4,5,6,7-tetrahydroindenyl]dichlorozirconium

[4-(η⁵-4'-trimethylsilylcyclopentadienyl)-2-trimethylsilyl-4,7-dimethyl-7-phenyl-η⁵-4,5,6,7-tetrahydroindenyl]dichlorozirconium

[4-(η⁵-3'-phenylcyclopentadienyl)-4,7,7-trimethyl-η⁵-4,5,6,7-tetrahydroindenyl]dichlorozirconium

[4-(η⁵-4'-phenylcyclopentadienyl)-4,7,7-trimethyl-η⁵-4,5,6,7-tetrahydroindenyl]dichlorozirconium

[4-(η⁵-3'-phenylcyclopentadienyl)-2-phenyl-4,7,7-trimethyl-η⁵-4,5,6,7-tetrahydroindenyl]dichlorozirconium

[4-(η⁵-4'-phenylcyclopentadienyl)-2-phenyl-4,7,7-trimethyl-η⁵- 4,5,6,7-tetrahydroindenyl]dichlorozirconium

[4-(η⁵-3"-phenylcyclopentadienyl)-4,7-dimethyl-7-phenyl-η⁵-4,5,6,7-tetrahydroindenyl]dichlorozirconium

[4-(η⁵-4'-phenylcyclopentadienyl)-4,7-dimethyl-7-phenyl-η⁵- 4,5,6,7-tetrahydroindenyl]dichlorozirconium

[4-(η⁵-3'-phenylcyclopentadienyl)-2-phenyl-4,7-dimethyl-7-phenyl-η⁵-4,5,6,7-tetrahydroindenyl]dichlorozirconium

[4-(η⁵-4'-phenylcyclopentadienyl)-2-phenyl-4,7-dimethyl-7-phenyl-(η⁵-4,5,6,7-tetrahydroindenyl]dichlorozirconium

[4-(η⁵-4'-methylcyclopentadienyl)-4,7,7-trimethyl-η⁵-4,5,6,7-tetrahydroindenyl]dichlorozirconium

[4-(η⁵-4'-methylcyclopentadienyl)-2-methyl-4,7,7-trimethyl-η⁵-4,5,6,7-tetrahydroindenyl]dichlorozirconium

[4-(η⁵-4'-methylcyclopentadienyl)-2-methyl-4,7-dimethyl-7-phenyl-η⁵-4,5,6,7-tetrahydroindenyl]dichlorozirconium

[4-(η⁵-4'-tert-butylcyclopentadienyl)-2-tert-butyl-4,7,7-trimethyl-η⁵- 4,5,6,7-tetrahydroindenyl]dichlorozirconium

[4-(η⁵-3'-tert-butylcyclopentadienyl)-2-tert-butyl-4,7,7-trimethyl-η⁵-4,5,6,7-tetrahydroindenyl]dichlorozirconium

[4-(η⁵-4'-tert-butylcyclopentadienyl)-4,7,7-trimethyl-η⁵-4,5,6,7-tetrahydroindenyl]dichlorozirconium

[4-(η⁵-3'-benzylcyclopentadienyl)-4,7,7-trimethyl-η⁵-4,5,6,7-tetrahydroindenyl]dichlorozirconium

[4-(η⁵-4'-benzylcyclopentadienyl)-4,7,7-trimethyl-η⁵-4,5,6,7-tetrahydroindenyl)]dichlorozirconium

[4-(η⁵-3'-benzylcyclopentadienyl)-2-benzyl-4,7,7-trimethyl-η⁵-4,5,6,7-tetrahydroindenyl]dichlorozirconium

[4-(η⁵-4'-benzylcyclopentadienyl)-2-benzyl-4,7,7-trimethyl-η⁵-4,5,6,7-tetrahydroindenyl]dichlorozirconium

[4-(η⁵-cyclopentadienyl)-4-butyl-7,7-dimethyl-η⁵-4,5,6,7-tetrahydroindenyl]dichlorozirconium

[4-(η⁵-cyclopentadienyl)-4-butyl-7-methyl-7-butyl-η⁵-4,5,6,7-tetrahydroindenyl]dichlorozirconium

[4-(η⁵-cyclopentadienyl)-4-methyl-7,7-dibutyl-η⁵-4,5,6,7-tetrahydroindenyl]dichlorozirconium

[4-(η⁵-cyclopentadienyl)-4-methyl-7-butyl-7-phenyl-η⁵-4,5,6,7-tetrahydroindenyl]dichlorozirconium

[4-(η⁵-cyclopentadienyl)-4-butyl-7-methyl-7-phenyl-η⁵-4,5,6,7-tetrahydroindenyl]dichlorozirconium

[4-(η⁵-3'-isopropylcyclopentadienyl)-2-isopropyl-4-butyl-7,7-dimethyl-η⁵-4,5,6,7-tetrahydroindenyl]dichlorozirconium

[4-(η⁵-4'-isopropylcyclopetadienyl)-2-isopropyl-4-butyl-7,7-dimethyl-η⁵-4,5,6,7-tetrahydroindenyl]dichlorozirconium

[4-(η⁵-3'-isopropylcyclopentadienyl)-2-isopropyl-4-butyl-7-butyl-7-methyl-η⁵-4,5,6,7-tetrahydroindenyl]dichlorozirconium

[4-(η⁵-4'-isopropylcyclopentadienyl)-2-isopropyl-4-butyl-7-methyl-7-phenyl-η⁵-4,5,6,7-tetrahydroindenyl]dichlorozirconium

[4-(η⁵-3'-isopropylcyclopentadienyl)-4-butyl-7-butyl-7-methyl-η⁵-4,5,6,7-tetrahydroindenyl]dichlorozirconium

[4-(η⁵-4'-isopropylcyclopentadienyl)-4-butyl-7-methyl-7-phenyl-η⁵-4,5,6,7-tetrahydroindenyl]dichlorozirconium

[4-(η⁵-cyclopentadienyl)-4,7-dimethyl-7-(2-propen-1-yl)-(η⁵-4,5,6,7-tetrahydroindenyl]dichlorozirconium

[4-(η⁵-3'-isopropylcyclopentadienyl)-4,7-dimethyl-7-(2-propen-1-yl)-(η⁵-4,5,6,7-tetrahydroindenyl]dichlorozirconium

[4-(η⁵-cyclopentadienyl)-4,7-dimethyl-7-(3-(9-borabicylo{3,3,1}non-8-ylpropyl)-(η⁵-4,5,6,7-tetrahydroindenyl]dichlorozirconium

[4-(η⁵-3'-isopropylcylopentadienyl)-4,7-dimethyl-7-(3-(9-borabicyclo{3,3,1}nonyl-β)propyl)-(η⁵-4,5,6,7-tetrahydroindenyl]dichlorozirconium

[4-(η⁵-4'-isopropylcyclopentadienyl)-4,7-dimethyl-7-(3-(9-borabiayclo{3,3,1}nonyl-β)propyl)-(η⁵-4,5,6,7-tetrahydroindenyl]dichlorozirconium

[4-(η⁵-3'-tert-butylcyclopentadienyl)-4,7-dimethyl-7-(3-(9-borabicyclo{3,3,1}nonyl-β)propyl)-(η⁵-4,5,6,7-tetrahydroindenyl]diohlorosiraium

[4-(η⁵-4'-tert-butyclopentadieayl)-4,7-dimethyl-7-(3- 9-borabicyclo{3,3,1}nonyl-β)propyl)-(η⁵-4,5,6,7-tetrahydroindenyl]dichlorozirconium

[4-(η⁵-3'-methylcyclopentadienyl)-4,7-dimethyl-7-(3-(9-borabicyclo{3,3,1}nonyl-β)propyl)-(η⁵-4,5,6,7-tetrahydroindenyl]dichlorozirconium

[4-(η⁵-3'-isopropyloyclopeutadienyl)-2-isopropyl-4,7-dimethyl-7-(3-(9-borabicyclo}3,3,1}nonyl-β)propyl)-(η⁵-4,5,6,7-tetrahydroindenyl]dichlorozirconium

[4-(η⁵-4'-isopropylcyclopentadienyl)-2-isopropyl-4,7-dimethyl-7-(3-(9-borabicyclo{3,3,1}nonyl-β)propyl)-(η⁵-4,5,6,7-tetrahydroindenyl]dichlorozirconium

[4-(η⁵-3'-ethylcyclopentadienyl)-4,7,7-trimethyl-η⁵-4,5,6,7-tetrahydroindenyl]dichlorozirconium

[4-(η⁵-4'-ethylcyclopentadienyl)-4,7,7-trimethyl-η⁵- 4,5,6,7-tetrahydroindenyl]dichlorozirconium

[4-(η⁵-3'-ethylcyclopentadienyl-2-ethyl-4,7,7-trimethyl-η⁵-4,5,6,7-tetrahydroindenyl]dichlorozirconium

[4-(η⁵-4'-ethylcyclopentadienyl)-2-ethyl-4,7,7-trimethyl-η⁵- 4,5,6,7-tetrahydroindenyl]dichlorozirconium

[4-(η⁵-3'-isopropylcyclopentadienyl)-2-phenyl-4,7,7,-trimethyl-η⁵-4,5,6,7-tetrahydroindenyl]dichlorozirconium

[4-(η⁵-4'-isopropyaycyclopantadienyl)-2-phenyl-4,7,7-trimethyl-η⁵-4,5,6,7-tetrahydroindonyl]dichlorozirconium

[4-(η⁵-3'-isopropylcyclopentadienyl)-2-methyl-4,7,7-trimethyl-η⁵- 4,5,6,7-tetrahydroindenyl]dichiorozirconium

[4-(η⁵-4'-isopropylcyalopentadienyl)-2-methyl-4,7,7-trimethyl-η⁵-4,5,6,7-tetrahydroindenyl]dichlorozirconium

[4-(η⁵-3'-isopropylaycyclopentadienyl)-2-phenyl-4,7,7-trimethyl-η⁵-4,5,6,7-tetrahydroindenyl]dichlorozirconium

[4-(η⁵-4'-isopropylcyalopentadienyl)-2-phenyl-4,7,7-trimethyl-η⁵-4,5,6,7-tetrahydroindenyl]dichlorozirconium

[4-(η⁵-2-indenyl)-4,7,7-trimethyl-η⁵-4,5,6,7-tetrahydroindenyl]dichlorozirconium

[4-(η⁵-2-(4,5,6,7-tetrahydro)indenyl)-4,7,7-trimethyl-η⁵-4,5,6,7-tetrahydroindenyl]dichlorozirconium

[4-(η⁵-2-indenyl)-2-methyl-4,7,7-trimethyl-η⁵-4,5,6,7-tetrahydroindenyl]dichlorozirconium

[4-(η⁵-2-(4,5,6,7-tetrahydro)indenyl)-2-isopropyl-4,7,7,-trimethyl-η⁵-4,5,6,7-tetrahydroindenyl]dichlorozirconium

[4-(η$^5$-2-indenyl) 2-phenyl-4,7,7-trimethyl-η$^5$-4,5,6,7-tetrahydroindenyl]dichlorozirconium
[4-(η$^5$-2-(4,5,6,7-tetrahydro)indenyl)-2- butyl-4,7,7-trimethyl-η$^5$-4,5,6,7-tetrahydroindenyl]dichlorozirconium
[4-(η$^5$-2-indenyl)-2-trimethylsilyl-4,7,7-trimethyl-η$^5$-4,5,6,7-tetrahydroindenyl]dichlorozirconium
[4-(η$^5$-2-(4,5,6,7-tetrahydro)indenyl)-2-trimethylsilyl-4,7,7-trimethyl-η$^5$-4,5,6,7-tetrahydroindenyl]dichlorozirconium
[4-(η$^5$-2-indenyl)-2-isopropyl-4,7,7-trimethyl-η$^5$-4,5,6,7-tetrahydroindenyl]dichlorozirconium
[4-(η$^5$-2-(4,5,6,7-tetrahydro)indenyl)-2-methyl-4,7,7-trimethyl-η$^5$- 4,5,6,7-tetrahydroindenyl]dichlorozirconium
[4-(η$^5$-2-indenyl)-2-butyl-4,7,7-trimethyl-η$^5$-4,5,6,7-tetrahydroindenyl]dichlorozirconium
[4-(η$^5$-2-(4,5,6,7-tetrahydro) indenyl)-2-phenyl-4,7,7-trimethyl-η$^5$-4,5,6,7-tetrahydroindenyl]dichlorozirconium
[4-(η$^5$-3'-isopropylcyclopentadienyl)-2-methyl-4,7,7-trimethyl-η$^5$-4,5,6,7-tetrahydroindenyl]dichlorozirconium
[4-(η$^5$-4'-isopropylcyclopentadienyl)-2-methyl-4,7,7-trimethyl-η$^5$-4,5,6,7-tetrahydroindenyl]dichlorozirconium
[4-(η$^5$-3'-isopropylcyclcpentadienyl)-4,7,7-trimethyl-η$^5$-4,5,6,7-tetrahydrofluorenyl]dichlorozirconium
[4-(η$^5$-4'-isopropylcyclcpentadienyl)-4,7,7-trimethyl-η$^5$-4,5,6,7-tetrahydrofluorenyl]dichlorozirconium
[4-(η$^5$-3'-isopropylcyclopentadienyl)-2-isopropyl-4,7,7-trimethyl-η$^5$-4,5,6,7-tetrahydrofluorenyl]dichlorozirconium
[4-(η$^5$-4'-isopropylcyalopentadienyl)-2-isopropyl-4,7,7-trimethyl-(η$^5$-4,5,6,7-tetrahydrofluorenyl]dichlorozirconium
[4-(η$^5$-3'-butylcyclopentadienyl)-4,7,7-trimethyl-η$^5$-4,5,6,7-tetrahydroindenyl]dichlorozirconium
[4-(η$^5$-4'-butylcyclopentadienyl)-4,7,7-trimethyl-η$^5$-4,5,6,7-tetrahydroindenyl]dichlorozirconium
[4-(η$^5$-3'-butylcyclopentadienyl)-2-isopropyl-4,7,7-trimethryl-(η$^5$-4,5,6,7-tetrahydroindenyl]dichlorozirconium
[4-(η$^5$-4'-butylcyclopentadienyl)-2-isopropyl-4,7,7-trimethyl-η$^5$-4,5,6,7-tetrahydroindenyl]dichlorozirconium
[4-(η$^5$-3'-butylcyclopentadienyl-2-butyl-4,7,7-trimethyl-η$^5$-4,5,6,7-tetrahydroindenyl)dichlorozirconium
[4-(η$^5$-4'-butylcyclopentadienyl)-2-butyl-4,7,7-trimethyl-η$^5$-4,5,6,7-tetrahydroindenyl]dichlorozirconium
[4-(η$^5$-3',4'-dimethylcyclopentadienyl)-4,7,7-trimethyl-η$^5$-4,5,6,7-tetrahydroindenyl]dichlorozirconium
[4-(η$^5$-3',4'-diisopropylcyclopentadienyl)-4,7,7-trimethyl-η$^5$- 4,5,6,7-tetrahydroindenyl]dichlorozirconium
[4-(η$^5$-3',4'-diphenylcyclopentadienyl)-2-isopropyl-4,7,7-trimethyl-η$^5$-4,5,6,7-tetrahydroindenyl]dichlorozirconium
[4-(η$^5$-3',4'-diethylcyclopentadienyl)-2-isopropyl-4,7,7-trimethyl-η$^5$-4,5,6,7-tetrahydroindenyl]dichlorozirconium
[4-(η$^5$-3',4'-dibutylcyclopentadienyl)-2-isopropyl-4,7,7-trimethyl-(η$^5$-4,5,6,7-tetrahydroindenyl]dichlorozirconium
[4-(η$^5$-3'-methyl-4'-phenylcyclopentadienyl)-4,7,7-trimethyl-η$^5$-4,5,6,7-tetrahydroindenyl]dichlorozirconium
[4-(η$^5$-3'-ethyl-4'-phenylcyclopentadienyl)-4,7,7-trimethyl-η$^5$-4,5,6,7-tetrahydroindenyl]dichlorozirconium
[4-(η$^5$-3'-isopropyl-4'-phenylcyclopentadienyl)-4,7,7-trimethyl-(η$^5$-4,5,6,7-tetrahydroindenyl]dichlorozirconium
[4-(η$^5$-3'-methyl-4'-isopropylcyclopentadienyl)-4,7,7-trimethyl-η$^5$-4,5,6,7-tetrahydroindenyl]dichlorozirconium
[4-(η$^5$-3-t-butylcyclopentadienyl)-4,6,6-trimethyl(η$^5$-2-t-butyl)-4,5-tetrahydropentalene)dichlorozirconium
[4-(η$^5$-cyclopentadienyl)-4,6,6-trimethyl(η$^5$-4,5-tetrahydropentalene))dichlorozirconium
silicon-bis(η$^5$-(2-propanediyl)cyclopentadienyl-)dichlorozirconium
silicon-bis(η$^5$-(2-propanediyl)cyclopentadienyl-)dichlorozirconium
germanium-bis(η$^5$-(2-propanediyl)-2-methylcyclopentadienyl)dichlorozirconium
[4-(η$^5$-3'-methyl-4'-naphthylcyclopentadienyl)-4,7,7-trimethyl-η$^5$-4,5,6,7-tetrahydroindenyl]dichlorozirconium
[4-(η$^5$-3'-methyl-4'-butylcyclopentadienyl)-4,7,7-trimethyl-η$^5$-4,5,6,7-tetrahydroindenyl]dichlorozirconium The nomenclature of the abovementioned novel compounds is illustrated with reference to the compound [4-(η$^5$-4'-methylcyclopentadienyl)-4,7,7-trimethyl(η$^5$-4,5,6,7-tetrahydroindenyl)]dichlorozirconium. The ring system bridging the two cyclopentadienyl ligands of this compound contains six ring carbon atoms (C4, C5, C6, C7, C8 and C9) and three methyl substituents. One cyclopentadienyl group is simply fused to the ring system, and a second is a substituent on the ring system.

The compounds mentioned below are named in accordance with IUPAC nomenclature.
[η$^5$-9-cyclopentadienyl)tricyclo[6.1.1.0$^{2,6}$]deca-2,5-dienyl]dichlorotitanium,
[η$^5$-9-(η$^5$-cyclopentadienyl)tricyclo[6.1.1.0$^{2,6}$]deca-2,5-dienyl]dichlorozirconium,
[η$^5$-7-methyl-9-(η$^5$-cyclopentadienyl)tricyclo-[6.1.1.0$^{2,6}$]deca-2,5-dienyl]dichlorotitanium,
[η$^5$-7-methyl-9-(η$^5$-cyclopentadienyl)tricyclo-[6.1.1.0$^{2,6}$]deca-2,5-dienyl]dichlorozirconium,
[η$^5$-9-methyl-9-(η$^5$-cyclopentadienyl)tricyclo-[6.1.1.0$^{2,6}$]deca-2,5-dienyl]dichlorotitanium,
[η$^5$-9-methyl-9-(η$^5$-cyclopentadienyl)tricyclo-[6.1.1.0$^{2,6}$]deca-2,5-dienyl]dichlorozirconium,
[η$^5$-10-(η$^5$-cyclopentadienyl)tricyclo[5.2.1.0$^{2,6}$]deca-2,5-dienyl]dichlorotitanium,
[η$^5$-10-(η$^5$-cyclopentadienyl)tricyclo[5.2.1.0$^{2,6}$]deca-2,5-dienyl]dichlorozirconium,
[η$^5$-10-methyl-10-(η$^5$-cyclopentadienyl)tricyclo-[5.2.1.0$^{2,6}$]deca-2,5-dienyl]dichlorotitanium,
[η$^5$-10-methyl-10-(η$^5$-cyclopentadienyl)tricyclo-[5.2.1.0$^{2,6}$]deca-2,5-dienyl]dichlorozirconium,
[η$^5$-9-(η$^5$-cyclopentadienyl)tricyolo[5.2.2.0$^{2,6}$]undeca-2,5-dienyl]dichlorotitanium,
[η$^5$-9-(η$^5$-cyclopentadienyl)tricyclo[5.2.2.0$^{2,6}$]undeca-2,5-dienyl]dichlorozirconium,
[η$^5$-9-methyl-9-(η$^5$-cyclopentadienyl)tricyclo[5.2.2.0$^{2,6}$]-undeca-2,5-dienyl]dichlorotitanium,
[η$^5$-9-methyl-9-(η$^5$-cyclopentadienyl)tricylo[5.2.2.0$^{2,6}$]-undeca-2,5-dienyl]dichlorozirconium
[η$^5$-10-(η$^5$-3'-methylcyclopentadienyl)tricyclo[5.2.1.0$^{2,6}$]-deca-2,5-dienyl]dichlorotitanium,
[η$^5$-10-(η$^5$-3'-methylcyclopentadienyl)tricyclo[5.2.1.0$^{2,6}$]-deca-2,5-dienyl]dichlorozirconium,
[η$^5$-10-methyl-10-(η$^5$-3'-methylcyolopentadienyl)tricyclo[5.2.1.0$^{2,6}$]deca-2,5-dienyl]dichlorotitanium,
[η$^5$-10-methyl-10-(η$^5$-3'-methylayclopentadienyl)tricyclo[5.2.1.0$^{2,5}$]deca-2,5-dienyl]dichlorozirconium,

[η⁵-4-methyl-10-(η⁵-3'-methylcyclopentadienyl)tricyclo-[5.2.1.0²,⁶]deca-2,5-dienyl]dichlorotitanium,
[η⁵-4-dimethyl-10-(η⁵-3'-methylcyclopentadienyl)tricyclo[5.2.1.0²,⁶]deca-2,5-dienyl]dichlorozirconium,
[η⁵-4,10-dimethyl-10-(η⁵-3'-methylcyclopentadienyl)tricyclo 5.2.1.0²,⁶]deca-2,5-dienyl]dichlorotitanium,
[η⁵-4,10-dimethyl-10-(η⁵-3'-methylcyclopentadienyl)tricyclo [5.2.1.0²,⁶]deca-2,5-dienyl]dichlorozirconium,
[η⁵-5-methyl-10-(η⁵-3'-methylcyclopentadienyl)tricyclo-[5.2.1.0²,⁶]deca-2,5-dienyl]dichlorotitanium,
[η⁵-5-methyl-10-(η⁵-3'-methylcyclopentadienyl)tricyclo-[5.2.1.0²,⁶]deca-2,5-dienyl]dichlorozirconium,
[η⁵-5,10-dimethyl-10-(η⁵-3'-methylcyclopentadienyl)-tricyclo[5.2.1.0²,⁶]deca-2,5-dienyl]dichlorotitanium,
[η⁵-5,10-dimethyl-10-(η⁵-3'-methylcyclopentadienyl)-tricyclo[5.2.1.0²,⁶]deca-2,5-dienyl]dichlorozirconium.

The preparation of the metallocenes according to the invention is intended to be illustrated by the reaction scheme below with reference to metallocenes of the formula VI in which $M^4$ is a metal from main group Ia, IIa or IIIa.

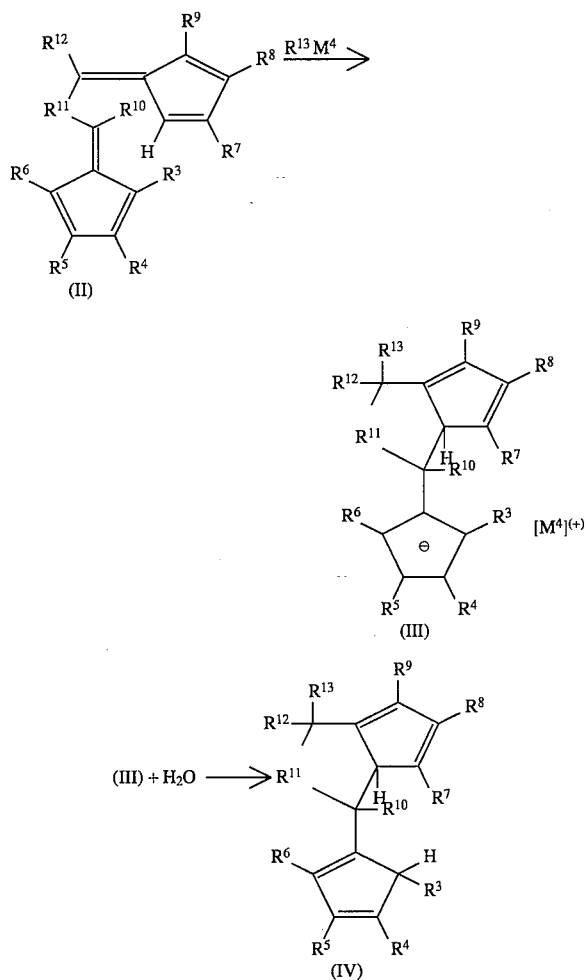

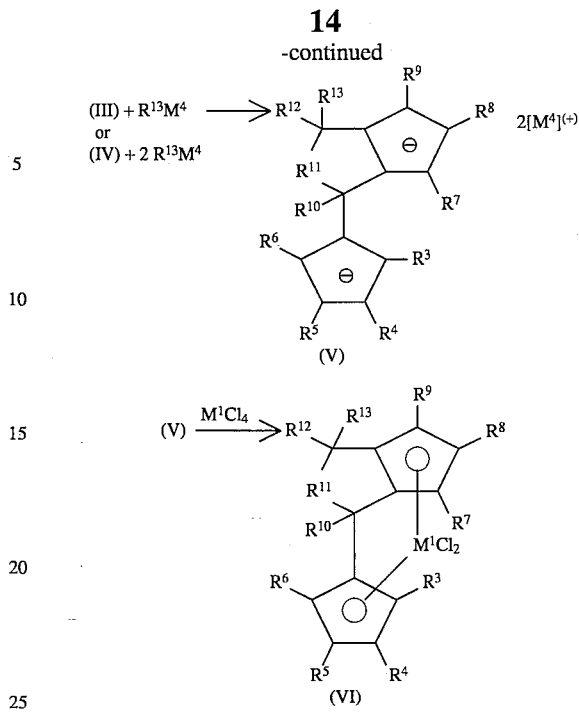

The difulvenes of the formula II are prepared from diketones (Chem. Ber. 114, 1226 (1981), ibid 109, 3426 (1976), ibid 107, 2453 (1974)) or ketoaldehydes by methods known from the literature (J. Org. Chem. 57 (1992) 2504; ibid, 49 (1984) 1849; Chimia, 46 (1992) 377).

The conversion of the difulvene II into the ligand system of the formula III is carried out by reaction with an organometallic compound (such as, for example, methyllithium, butyllithium or phenyllithium) or Grignard reagents.

The salts of the formula III can be converted directly into the corresponding dianion compounds of the formula V by deprotonation, for example using butyllithium. Hydrolysis of compound III results in the formation of the biscyclopentadienyl compound IV, which is produced as a constitutional isomer mixture and can be purified by chromatography. Double deprotonation of IV using, for example, butyllithium gives the dianion compound of the formula V.

Conversion into the bridged metallocenes of the formula VI and isolation of the desired complexes is known in principle. To this end, the dianion of the formula V is reacted with the corresponding metal halide, such as, for example, zirconium tetrachloride, in an inert solvent. The metallocenes of the formula VI can also be synthesized directly from the difulvenes of the formula II without isolation of the intermediates.

Suitable solvents are aliphatic or aromatic solvents, such as, for example, hexane or toluene, ethereal solvents, such as, for example, tetrahydrofuran or diethyl ether, or halogenated hydrocarbons, such as, for example, methylene chloride, or halogenated aromatic hydrocarbons, such as, for example, o-dichlorobenzene.

The biscyclopentadienyl compounds of the formula IV in which at least one of the radicals $R^3$ to $R^1$ and at least one of the radicals $R^7$ to $R^9$ is hydrogen and at least one of the radicals $R^3$ to $R^9$ is not hydrogen can be converted into the fulvenes of the formula IVa or IVb by methods known from the literature. This is intended to be illustrated by the reaction scheme below, where $R^{17}$, $R^{18}$, $R^{20}$ and $R^{21}$ are identical or different and are as defined for $R^{10}$.

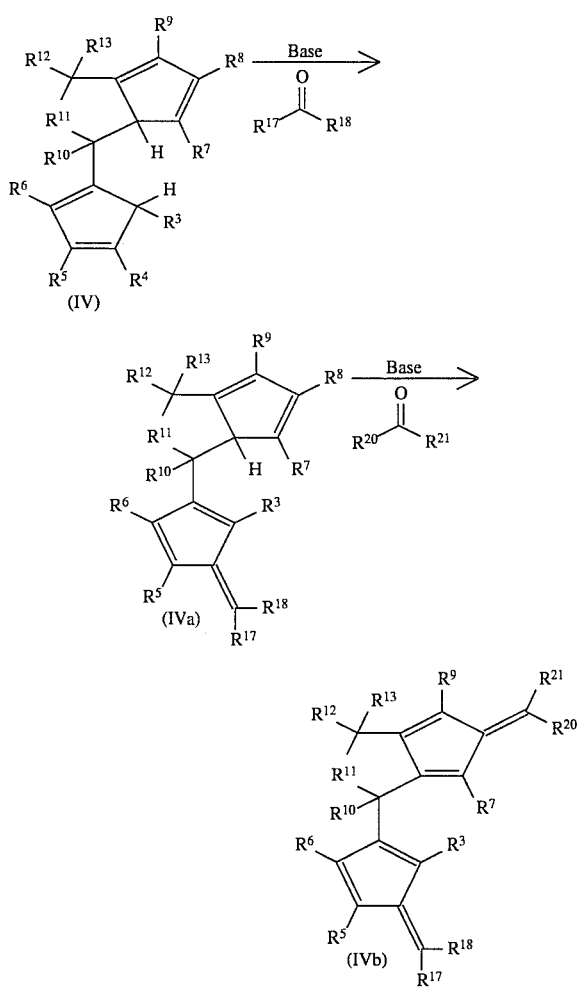

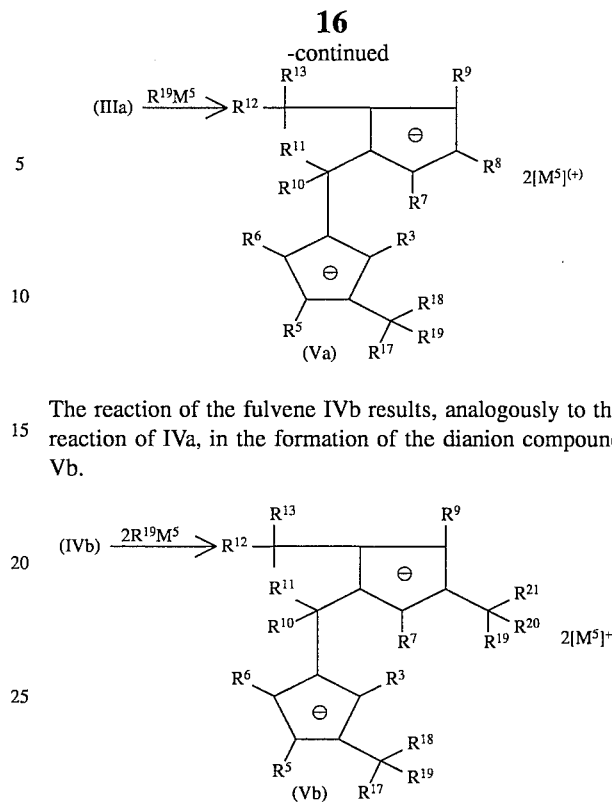

The reaction of the fulvene IVb results, analogously to the reaction of IVa, in the formation of the dianion compound Vb.

Reaction of the fulvene IVa with organometallic compounds of the formula $R^{19}M^5$ (where $R^{17}$, $R^{18}$, $R^{19}$, $R^{20}$ and $R^{21}$ are identical or different and are defined as for $R^{10}$; $M^5$ is as defined for $M^4$) results in the formation of the monoanion compound IIIa. Use of two equivalents of $R^{19}M^5$ results directly in the formation of the dianion compound Va.

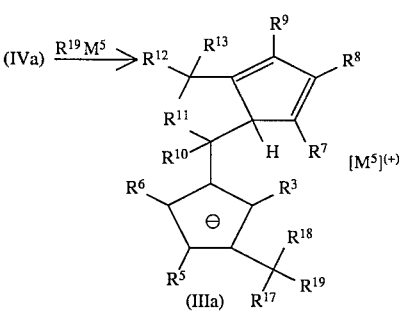

The biscyclopentadienyl anions of the formula V can be reacted with compounds $R^{22}{}_p M^6 X$, in which
$M^6$ is an element from main group III–V,
X is a leaving group, such as halogen, tosylate or triplate,
$R^{22}$ is as defined for $R^{10}$, and
p is an integer from 1 to 5.
This is illustrated by the reaction scheme below:

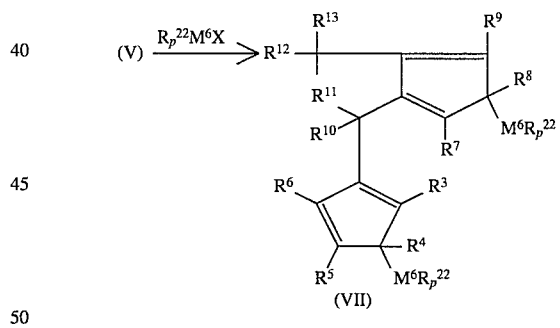

The compounds of the formula VII in which at least one of the radicals $R^3$ to $R^6$ and at least one of the radicals $R^7$ to $R^9$ is hydrogen can be converted into the metallocenes according to the invention.

The salts of the formula IIIa can be converted directly into the corresponding dianion compounds of the formula Va by deprotonation using, for example, butyllithium. Conversion into the bridged metallocenes of the formula I is carried out correspondingly to the reaction of V into VI.

Another way of forming the metallocene compounds according to the invention comprise reacting monocyclic or polycyclic ring systems to which a cyclopentadienyl group is fused and which carry functional groups which can serve as leaving groups in substitution reactions (such as, for example, bromide or tosylate) with, for example, cyclopentadienyl- or indenyllithium compounds.

The metallocenes employed in the process according to the invention are highly active catalyst components for the polymerization of olefins. Depending on the substitution pattern of the ligands, the metallocenes can be formed as an isomer mixture. The metallocenes are preferably employed in isomerically pure form. The use of the racemate is in most cases sufficient.

However it is also possible to use the pure enantiomer in the (+) or (−) form. Using the pure enantiomers, an optically active polymer can be prepared. However, the configuration-isomeric forms of the metallocenes should be separated, since the polymerization-active center (the metal atom) in these compounds produces a polymer having different properties. For certain applications, for example soft moldings, this may be entirely desirable.

Preference is given in the process according to the invention to the homopolymerization or copolymerization of one or more olefins of the formula $R^a$—CH=CH—$R^b$, in which $R^a$ and $R^b$ are identical or different and are a hydrogen atom or a hydrocarbon radical having 1 to 20 carbon atoms, in particular 1 to 10 carbon atoms, or $R^a$ and $R^b$, together with the atoms connecting them, form one or more rings. Examples of such olefins are 1-olefins, such as ethylene, propylene, 1-butane, 1-pentene, 1-hexene, 4-methyl-1-pentene or 1-octane, styrene, cyclic and acyclic dienes, such as 1,3-butadiene, isoprene, 1,4-hexadiene, norbornadiene, vinylnorbornene or 5-ethylidenenorbornene. Preference is given in the process according to the invention to the homopolymerization of ethylene or the copolymerization of ethylene with one or more 1-olefins having 3 to 20 carbon atoms, such as propylene, and/or one or more dienes having 4 to 20 carbon atoms, such as 1,3-butadiene.

The polymerization is preferably carried out at a temperature of from −60° to 250° C., particularly preferably from 50° to 20° C. The presuure is preferably from 0.5 to 2000 bar, particularly preferably from 5 to 64 bar.

The polymerization can be carried out in solution, in bulk, in suspension or in the gas phase, continuously or batchwise, and in one or more steps. A preferred embodiment is gas-phase polymerization.

The catalyst employed in the process according to the invention preferably contains a metallocene compound. It is also possible to employ mixtures of two or more metallocene compounds, for example for the preparation of polyolefins having a broad or multimodal molecular weight distribution.

In principle, the cocatalyst in the process according to the invention can be any compound which, owing to its Lewis acidity, can convert the neutral metallocene to a cation and stabilize it (labile coordination). In addition, the cocatalyst or the anion formed thereby should not undergo any further reactions with the metallocene cation formed (EP 427 697). The cocatalyst is preferably an aluminum compound and/or a boron compound.

The boron compound preferably has the formula $R^{25}{}_xNH_{4-x}BR^{26}{}_4$, $R^{25}{}_xPH_{4-x}BR^{26}{}_4$, $R^{25}{}_3CBR^{26}{}_4$ or $BR^{26}{}_3$, in which x is a number from 1 to 4, preferably 3, the radicals $R^{25}$ are identical or different, preferably identical, and are $C_1$–$C_{10}$-alkyl or $C_6$–$C_{18}$-aryl, or two radicals $R^{25}$, together with the atoms connecting them, form a ring, and the radicals $R^{26}$ are identical or different, preferably identical, and are $C_6$–$C_{18}$-aryl, which may be substituted by alkyl, haloalkyl or fluorine. In particular, $R^{25}$ is ethyl, propyl, butyl or phenyl and $R^{26}$ is phenyl, pentafluorophenyl 3,5-bistrifluoromethylphenyl, mesityl, xylyl or tolyl (EP 277 003, EP 277 004 and EP 426 638).

The cocatalyst is preferably an aluminum compound, such as aluminoxane and/or an alkylaluminum compound.

The cocatalyst is particularly preferably an aluminoxane, in particular of the formula IIa for the linear type and/or of the formula IIb for the cyclic type,

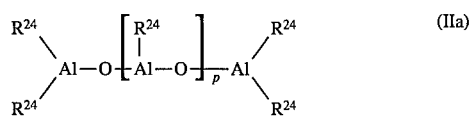

where, in the formulae IIa and IIb, the radicals $R^{24}$ are identical or different and are hydrogen or a $C_1$–$C_{20}$-hydrocarbon groups, such as a $C_1$–$C_{18}$-alkyl group, a $C_6$–$C_{18}$-aryl group or benzyl, and p is an integer from 2 to 50, preferably 10 to 35.

The radicals $R^{24}$ are preferably identical and are preferably hydrogen, methyl isobutyl, phenyl or benzyl, particularly preferably methyl.

If the radicals $R^{24}$ are different, they are preferably methyl and hydrogen or alternatively methyl and isobutyl, where hydrogen or isobutyl in preferably present to the extent of 0.01–40% (of the radicals $R^{24}$).

The processes for the preparation of the aluminoxanes are known. The precise spatial structure of the aluminoxanes is not known (J. Am. Chem. Soc. (1993) 115, 4971). It is conceivable, for example, for chains and rings to be connected to form extended two-dimensional or three-dimensional structures.

Irrespective of the preparation method, all aluminoxzane solutions have in common a varying content of unreacted aluminum starting compound, which is in free form or as an adduct.

It is possible to preactivate the metallocene compound by means of a cocatalyst, in particular aluminoxane before use in the polymerization reaction. This significantly increases the polymerization activity. The preactivation of the metallocene compound is preferably carried out in solution. The metallocene compound is preferably dissolved in a solution of the aluminokane in an inert hydrocarbon. Suitable inert hydrocarbons are aliphatic or aromatic hydrocarbons. Toluene is preferred.

The concentration of the aluminoxane in the solution is in the range from about 1% by weight to the saturation limit, preferably from 5 to 30% by weight in each case based on the total amount of solution. The metallocene can be employed in the same concentration, but is preferably employed in an amount of from $10^{-4}$ to 1 mol per mol of aluminoxane. The preactivation is carried out for from 5 minutes to 60 hours, preferably for from 5 to 60 minutes. The temperature is −78° to 100° C., preferably from 0° to 70° C.

The metallocene compound is preferably used in a concentration, based on the transition metal, of from $10^{-3}$ to $10^{-8}$ mol, preferably from $10^{-4}$ to $10^{-7}$ mol of transition metal per dm$^3$ of solvent or per dm$^3$ of reactor volume. The aluminoxane is preferably used in a concentration of from $10^{-6}$ to $10^{-1}$ mol, preferably from $10^{-5}$ to $10^{-2}$ mol, per dm$^3$ of solvent or per dm$^3$ of reactor volume. The other catalysts mentioned are used in approximately equimolar amounts with respect to the metallocene compound. In principle, however, higher concentrations are also possible.

The aluminoxane can be prepared in various ways by known processes. One of the methods is for example, to react an aluminum hydrocarbon compound and/or a hydridoaluminum hydrocarbon compound with water (in gas, solid, liquid or bound form—for example as water of crystallization) in an inert solvent (such as, for example toluene). In order to prepare an aluminoxane containing different radicals $R^{24}$, two different trialkylaluminum compounds, for example, according to the desired composition are reacted with water.

Irrespective of the preparation method, all aluminoxane solutions have in common a varying content of unreacted aluminum starting compound, which is in free form or as an adduct.

It is possible to preactivate the metallocene by means of a cocatalyst, in particular aluminoxane, before use in the polymerization reaction. This significantly increases the polymerization activity and improves the grain morphology. Preactivation of the transition-metal compound is carried out in solution. The metallocene is preferably dissolved in a solution of the aluminoxane in an inert hydrocarbon. Suitable inert hydrocarbons are aliphatic or aromatic hydrocarbons. Toluene is preferred.

The concentration of the aluminoxane in the solution is in the range from about 1% by weight to the saturation limit, preferably from 5 to 30% by weight in each case based on the total amount of solution. The metallocene can be employed in the same concentration, but is preferably employed in an amount of from $10^{-4}$ to 1 mol per mol of aluminoxane. The preactivation is carried out for from 5 minutes to 60 hours, preferably for from 5 to 60 minutes. The temperature is preferably from −78° to 150° C., preferably from 0° to 80° C.

In order to remove catalyst poisons present in the olefin, purification using an alkylaluminum compound, preferably trimethylaluminum or triethylaluminum, is advantageous. This purification can be carried out either in the polymerization system itself, or the olefin is brought into contact with the aluminum compound before introduction into the polymerization system and is subsequently removed again.

Hydrogen can be added in the novel process as a molecular weight regulator and/or in order to increase the catalyst activity. This allows low-molecular-weight polyolefins, such as waxes, to be obtained.

In the process according to the invention, the metallocene compound is preferably reacted with the cocatalyst outside the polymerization reactor in a separate step using a suitable solvent. At the same time it can be applied to a support.

The metallocene compound can be used to carry out a prepolymerization in the novel process, preferably using the (or one of the) olefin(s) employed in the polymerization.

The catalyst employed in the process according to the invention can be supported. The supporting allows, for example, the particle morphology of the resultant polyolefin to be controlled. The metallocene compound can either be reacted first with the support and subsequently with the cocatalyst, or the cocatalyst can first be supported and subsequently reacted with the metallocene compound. It is also possible to support the product of the reaction of the metallocene compound and the cocatalyst. Examples that are suitable to the support materials are silica gels, aluminum oxides, solid aluminoxane or other inorganic support materials, such as, for example, magnesium chloride. Another suitable support material is a polyolefin powder in finely divided form. The supported cocatalyst can be prepared, for example, as described in EP 567 952.

Suitable support materials are, for example, silica gels, aluminum oxides, solid aluminoxane or other inorganic support materials, such as, for example, magnesium chloride. Another suitable support material is a polyolefin powder in finely divided form.

It is preferred to apply the cocatalyst, for example aluminoxane to a support, such as, for example, silica gels, aluminu oxides, solid aluminoxane, other inorganic support materials or alternatively a polyolefin powder in finely divided form, and then to react it with the metallocene.

Inorganic supports which can be employed are oxides produced by flame pyrolysis by combustion of element halides in an oxyhydrogen flame, or can be prepared as silica gels in certain particle size distributions and particle shapes.

The preparation of the supported cocatalyst can be carried out, for example, as described in EP 578 838 in the following way in an explosion-proofed stainless-steel reactor with a 60 bar pump system, with inert-gas supply, temperature control by jacket cooling and second cooling circuit via a heat exchanger on the pump system. The pump system aspirates the reactor contents via a connection in the reactor bottom and forces them into a mixer and back into the reactor through a rising line via a heat exchanger. The mixer is designed so that the feed contains a narrowed tube cross section, where an increased flow rate is produced and in whose turbulence zone a narrow feed line is installed axially and against the flow direction and which can be fed—in pulses—in each case with a defined amount of water under 40 bar of argon. The reaction is monitored via a sampler in the pump circuit.

In principle, however, other reactors are also suitable.

In the above-described reactor having a volume of 16 $dm^3$, 5 $dm^3$ of decane are introduced under inert conditions. 0.5 $dm^3$ (=5.2 mol) of trimethylaluminum are added at 25° C. 250 g of silica gel SD 3216-30 (Grace AG) which had previously been dried at 120° C. in an argon fluidized bed are than metered into the reactor through a solids funnel and homogenously distributed with the aid of the stirrer and the pump system. A total amount of 76.5 g of water is introduced to the reactor in portions of 0.1 $cm^3$ every 15 seconds over the course of 3.25 hours. The pressure, caused by argon and the evolved gases, is kept constant at 10 bar by a pressure-regulation valve. When all the water has been introduced, the pump system is switched off and the stirring is continued for a further 5 hours at 25° C.

The supported cocatalyst prepared in this way is employed as a 10% strength suspension in n-decane. The aluminum content is 1.06 mmol of Al per $cm^3$ of suspension. The isolated solid contains 31% by weight of aluminum, and the suspension medium contains 0.1% by weight of aluminum.

Further ways of preparing a supported cocatalyst are described in EP 578 838.

The metallocene according to the invention is then applied to the supported cocatalyst by stirring the dissolved metallocene with the supported cocatalyst. The solvent is removed and replaced by a hydrocarbon in which both the cocatalyst and the metallocene are insoluble.

The reaction to give the supported catalyst system is carried out at a temperature of from −20° to 120° C., preferably at from 0° to 100° C., particularly preferably at from 15° to 40° C. The metallocene is reacted with the supported cocatalyst by combining the cocatalyst as a from 1 to 40% strength by weight suspension, preferably with a from 5 to 20% strength by weight suspension, in an aliphatic, inert suspension medium, such as n-decane, hexane, heptane or diesel oil, with a solution of the metallocene in an inert solvent, such as toluene, hexane, heptane or dichloromethane, or with the finely ground solid of the metallocene. Conversely, it is also possible to reaat a solution of the meltallocene with the solid of the cocatalyst.

The reaction is carried out by vigorous mixing, for example by stirring at a molar Al/M$^1$ ratio of from 100/1 to 10,000/1, preferably from 100/1 to 3,000/1, and for a reaction time of from 5 to 120 minutes, preferably from 10 to 60 minutes, particularly preferably from 10 to 30 minutes, under inert conditions.

During the reaction time for the preparation of the supported catalyst system, in particular on use of the metallocenes according to the invention having absorption maxima in the visible region, changes in the color of the reaction mixture occur which can be used to monitor the progress of the reaction.

When the reaction time is complete, the supernatant solution is separated off, for example by filtration or decanting. The solid which remains is washed from 1 to 5 times with an inert suspension medium, much as toluene, n-decane, hexane, diesel oil or dichioromethane, in order to remove soluble constituents in the catalyst formed, in particular to remove unreacted and thus soluble metallocene.

The supported catalyst system prepared in this way can, either dried in vacuum as a powder or still with adhering solvent, he resuspended and watered into the polymerization system as a suspension in one of the abovementioned inert suspension media.

If the polymerization is carried out as a suspension or solution polymerization, an inert solvent which is customary for the Ziegler low-pressure process is used. For example, the polymerization is carried out in an aliphatic or cycloaliphatic hydrocarbon; examples which may he mentioned are propane, butane, hexane, heptane, isooctane, cyclohexane and methylcyclohexane. It is furthermore possible to use a benzine or hydrogenated polymetization is preferably carried out in the liquid monomer.

Before addition of the catalyst in particular of the supported catalyst system (comprising a metallocene according to the invention and a supported cocatalyst or a metallocene according to the invention and an organo-aluminum compound on a polyolefin powder in finely divided form), another alkylaluminum compound, such as, for example, trimethylaluminum, triethylaluminum, triisobutylaluminum, trioctylaluminum or isoprenyl-aluminum, may additionally be introduced into the reactor in order to render the polymerization system inert (for example to remove catalyst poisons present in the olefin). This compound ia added to the polymerization system in a concentration of from 100 to 0.01 mmol of Al per kg of reactor contents. Preference is given to trissobutylaluminum and triethylaluminum in a concentration of from 10 to 0.1 mmol of Al per kg of reactor contents. This allows the molar Al/M$^1$ ratio to be selected at a low level in the synthesis of a supported catalyst system.

If inert solvents are used, the monomers are metered in in gas or liquid form.

The polymerization can have any desired duration, since the catalyst system to be used in the process according to the invention exbits only a slight time-dependent drop in polymerization activity.

The metallocenes employed in the process according to the invention are suitable for the preparation of polyolefins of reduced crystallinity, increased impact strength, increased transparency, high flowability at the processing tempterature and reduced melting point.

The main application of such polyolefins are plasticizer and lubricant formulations, hot-melt adhesive applications, coatings, seals, insulation, slush-molding compositions or sound insulation amaterials.

By using hydrogen or by increasing the polymerization temperature, polyolefins of low molecular weight, such as waxes, can also be obtained their hardness or melting point can be varied by means of the comonomer content.

Conversely, selection of the polymerization conditions also allows preparation of high-molecular-weight polyolefins, which are suitable as thermoplastic materials. These are particularly suitable for the production of moldings, such as films, sheets or large hollow elements (for example pipes).

Selection of the polymerization process and the type(s) of and amount(s) of the comonomer allows the preparation of olefin copolymers having elastomeric properties, such as, for example, ethylene-propylene-1,4,hexadiene terpolymers.

The examples below serve to illustrate the invention in greater detail.

Organometallic compounds were prepared and handled under a blanket of argon with exclusion of air and moisture (Schlenk technique). All the solvents required were rendered absolute before use by boiling for a number of hours over a suitable desiccant followed by distillation under argon.

The diketones and ketoaldehydes employed as starting compounds were prepared by methods known from the literature. Cyclopentadiene and methylcyclopentadiene were obtained by cracking dimers and were stored at −35° C.

The determination of the Al/CH$_3$ ratio in the aluminoxane was carried out by decomposition of the sample using $H_2SO_4$ and determination of the volume of the resultant hydrolysis gases under standard conditions and by complexometric titration of the aluminum in the sample, then dissolved, by the Sahwerzenbach method.

The compounds were characterized by $^1$H-NMR, $^{13}$C-NMR and IR spectroscopy.

The polymer melting points and heats of fusion given are taken from a DSC measurement for the 2nd melting at a heating rate of 10°/min.

Toluene-soluble methylaluminoxane for the comparative examples is purchased from WITCO as a 10% strength toluene solution and, according to aluminum deterermination contains 36 mg of Al/ml.

The comonomer incorporation is determined by $^{13}$C-NMR by the Randall method (Macromolecules 1994, 27, 2120).

The examples below serve to illustrate the invention, but do not represent a limitation:

A. Preparation of the Bisfulvenes II

EXAMPLE 1a

Synthesis of 2,5-bis(2,4-cyclopentadien-1-ylidene)hexane

In a modified reaction procedure [a], 11.0 g (96.3 mmol) of 2,5-hexanedione and 12.7 g (193 mol) of freshly cracked cyclopentadiene are dissolved in 60 ml of methanol, the solution is cooled to 0° C., and 8.60 g (121 mmol) of pyrrolidine are added. The reaction solution is stirred at 0° C. for 90 minutes, hydrolyzed using 5 ml of glacial acetic aaid and 50 ml of water, and extracted twice with 70 ml of diethyl ether in each case, and the combined organic phases are washed with saturated sodium chloride solution and dried over magnesium sulfate, giving, after removal of the solvent in vacuo, 18.0 g (89%) of the difulvene as an orange-red, oily residue.

[a]=M. S. Erickson, J. M. Cronan, J. G. Garcia, M. L. McLaughlin, J. Org. chem. 57 (1992) 2504–2508. K. J. Stone, R. D. Little, J. Org. Chem. 49 (1984) 1849–1853.

EXAMPLE 1b

Synthesis of 2,5-bis(cyclopenta-2,4-dien-1-ylidene)undecane

A solution of 3.50 g (19.9 mmol) of 2,5-undecanedione in 100 ml of methanol and 10 ml of tetrahydrofuran is cooled to 0° C., and 3.92 ml (3.14 gl 47.5 mmol) of freshly cracked cyclopentadiene are added. 6.28 ml (5.40 g, 76.0 mmol) of freshly distilled pyrrolidine are then added dropwise to the orange-red, clear reaction solution over the course of 10 minutes. The reaction solution changes color to dark red within 10 minutes. The mixture is then allowed to warm to room temperature and stirred for a further 3 days in order to complete the reaction. For work-up, the pyrrolidine is neutralized using 4 ml of glacial acetic acid and hydrolyzed using 100 ml of water. The mixture is extracted twice with 100 ml of pentane in each case, the combined organic phases are washed a number of times with saturated, aqueous sodium chloride solution and dried over magnesium sulfate. Removal of the solvent in vacuo gives the cyclopentadienylidene (2) as a dark red oil in a crude yield of 78% (4.16 g).

Purification by column chromatography over silica gel acid deactivated by means of triethylamine, and pentane:diethyl ether (100:1) as eluting solvent mixture gives the difulvene (2) as an orange oil.

B. Synthesis of the Bridged Biscyclopentadienyl Anions V

EXAMPLE 2

Synthesis of [4-($\eta^5$-cyclopentadienyl)-4,7,7-trimethyl-($\eta^5$-4,5,6,7-tetrahydroindenyl)]dilithium 62.4 ml (99.1 mmol) of an ethereal 1.60M methyllithium solution are slowly added dropwise at 0° C. with vigorous stirring to a solution of 10.0 g (47.5 mmol) of 2,5-bis(2,4-cyclopentadien-1-ylidene)hexane in 150 ml of diethyl ether. The mixture is allowed to warm to room temperature and is stirred for 24 hours, giving a beige precipitate. Filtration through a frit and repeated washing with pentane give 13.2 g (89%) of the dilithium salt as a beige powder coordinated with one mole-equivalent of diethyl ether.

EXAMPLE 3

Synthesis of 4-($\eta^5$-cyclopentadienyl)-4,7-dimethyl-7-phenyl($\eta^5$-4,5,6,7-tetrahydroindenyl)dilithium An ethereal solution of phenyllithium (83.4 ml 74.3 mol, 0.89M diethyl ether solution) is added dropwise at 0° C. to a solution of 7.10 g (33.7 mmol) of difulvene (Example 1) in 100 ml of diethyl ether. After about 5 minutes, a beige precipitate stars to deposit. The mixture is allowed to warm to room temperature, and is than stirred for a further 12 hours at 25° C. Filtration through a frit, repeated washing with pentane and drying in an oil-pump vacuum give the dilithium salt as a beige, very hydrolysis-sensitive powder in a yield of 82% (10.3 g).

EXAMPLE 4

Synthesis of 4-($\eta^5$-cyclopentadienyl)-4,7-dimethyl-7-butyl($\eta^5$-4,5,6,7-tetrahydroindenyl)dilithium A solution of 15.0 g (71.3 mmol) of difulvene (Example 1), dissolved in 100 ml of diethyl ether, is cooled to −30° C., and 94 ml (150 mmol) of a 1.60M solution of n-butyllithium in hexane is added slowly with vigorous stirring. A lemon-yellow precipitate forms. The mixture is allowed to warm to room temperature, and is stirred for a further 24 hours in order to complete the reaction. The resultant precipitate is then filtered off, washed several times with pentane and dried in an oil-pump vacuum, giving 23.0 g (91%) of the dilithium salt as a beige, very hydrolysis-sensitive powder to which one mole-equivalent of diethyl ether is coordinated.

C. Synthesis of the bridged cyclopantadiene IV

EXAMPLE 5

Synthesis of 7-cyclopentadienyl-4,4,7-trimethyl-4,5,6,7-tetrahydro-1H-indene 50 ml of degased water are added dropwise at 0° C. to a suspension of 7.35 g (23.5mmol) of the dilithium salt (Example 2) in 50 ml of diethyl ether. During this addition, the beige suspension disappears immediately, giving a clear, orange diethyl ether phase. The phases are subsequently separated in a separating funnel, the aqueous phase is extracted twice with 25 ml of diethyl ether in each case, and the combined organic phases are washed with 20 ml of a saturated sodium chloride solution. Drying over magnesium sulfate and removal of the solvent in vacuo give 5.1 g (96%) of the hydrolyzed product as an orange-red oil.

EXAMPLE 6

Preparation of 7-cyclopentadienyl-4,7-diethyl-4-phenyl-4,5,6,7-tetrahydro-1H-indene A yellow suspension, cooled to 0° C., of of 3.64 g (9.72 mmol) of the dilithium salt (Example 3) in 50 ml of diethyl ether is hydrolyzed by slow addition of 20 ml of degased water. During this addition, the suspension disappears, giving an orange, clear reaction solution. After the mixture has been extracted twice with 20 ml of diethyl ether in each case, the combined organic phases are washed several times with saturated, aqueous sodium chloride solution and dried over magnesium sulfate. Subsequent removal of the solvent in vacuo gives the hydrolyzed product as an orange oil in a yield of 94% (2.62 g).

EXAMPLE 7

Preparation of 7-cyclopentadienyl-4,7-dimethyl-4-butyl-4,5,6,7-tetrahydro-1H-indene A yellow suspension, cooled to 0° C. of 5.00 g (17.33 mmol) of the dilithium salt (Example 4) in 50 ml of diethyl ether is hydrolyzed by slow addition of 20 ml of degased water. During this addition, the suspension disappears, giving an orange, clear reaction solution. After the mixture has been extracted twice with 20 ml of diethyl ether in each case, the combined organic phases are washed several times with saturated, aqueous sodium chloride solution and dried over magnesium sulfate. Subsequent removal of the solvent in vacuo gives the hydrolyzed product as an orange oil in a yield of 96% (4.59 g).

D. Synthesis of bridged cyclopentadiene-fulvene ligands IVa by subsequent introduction of substituents (introduction of various radicals $R^{13}$, $R^{17}$, $R^{18}$, $R^{20}$, and $R^{21}$)

EXAMPLE 8a

Synthesis of 7-(3'-isopropyltdenecyclopenta-1,4-dienyl)-4,4,7-trimethyl-4,5,6,7-tetrahydro-1H-indene 7.70 g (34.0 mmol) of the cyclopentadienyltetrahydroindene (Example 5) are dissolved in 70 ml of methanol and cooled to 0° C. The orange-red reaction solution is subsequently treated successively with 2.91 g (51.0 mmol) of acetone and 4.83 g (68.0 mool) of pyrrolidine. The mixture is stirred at 0° C. for 5 hours and then, in order to complete the reaction, at room temperature for a further 2 hours, before the reaction is terminated by addition of 4 ml of glacial acetic acid. The red, clear reaction solution is hydrolyzed by means of 200 ml of water, and the yellow suspension is extracted 3 × with 50 ml of diethyl ether in each case. Repeated washing of the combined organic phases with saturated, aqueous sodium chloride solution and drying over magnesium sulfate give the fulvene as an orange-red, waxlike residue in a yield of 88% (8.00 g).

EXAMPLE 8b

Preparation of 4-cyclopentadienyl-4,7-dimethyl-7-allyl-4,5,6,7-tetrahydro-1H-indene 293 ml of a 0.60M solution of the allyl Grignard reagent (175 mmol) in diethyl ether are added dropwise over the course of 1 hour with vigorous stirring to a solution of 16.8 g (79.8 mmol) of 2,5-bis(2,4-cyclopentadien-1-ylidene)hexane (Example 1) dissolved in 100 ml of diethyl ether and 50 ml of tetrahydrofuran. When the addition is complete, the mixture is stirred overnight at room temperature, before the yellow-orange suspension is cooled to 0° C. and carefully hydrolyzed by means of aqueous, saturated ammonium chloride solution. The organic phase is separated off, washed three times with 50 ml of saturated, aqueous sodium chloride solution in each case and subsequently dried over magnesium sulfate. Removal of the solvent in an oil-pump vacuum gives 17.5 g of the product as an orange oil (87%).

E. Synthesis of the dianion complexes Va

EXAMPLE 9a

Synthesis of 4-[3'-t-Bu-($\eta^5$-cyclopentadienyl)]-4,7,7,-trimethyl ($\eta^5$-tetrahydroindenyl)dilithium During the reaction of the tetrahydroindenylfulvene (Example 8) with an ethereal solution of methyllithium (2 equivalents) at 0° C., an intense yellow precipitate is obtained after only a few seconds. The mixture is stirred at room temperature for a further 12 hours, filtered through a frit, washed with pentane and dried in an oil-pump vacuum, giving a dilithium salt, which is further reacted directly without further characterization.

EXAMPLE 9b

Synthesis of [4-$\eta^5$-cyclopentadienyl)-4,7-dimethyl-7-allyl ($\eta^5$-4,5,6,7-tetrahydroindenyl)]dilithium 10.5 g of the allyl Grignard product (Example 10) are dissolved in 100 ml of diethyl ether, the solution is cooled to 0° C., and 57.6 ml of n-butyllithium solution (1.60M in hexane, 92.0 mmol) are added dropwise. After the mixture has been stirred at room temperature for 18 hours, the yellow-beige residue is filtered off, washed several times with pentane and dried in an oil-pump vacuum. The dilithium salt is isolated in qualitative yield as a beige solid and is coordinated with one mole-equivalent of diethyl ether.

F. Synthesis of the metallocenes of formula I

EXAMPLE 10

Synthesis of 4-($\eta^5$-cyclopentadienyl)-4,7,7-trimethyl($\eta^5$-4,5,6,7-tetrahydroindenyl)]dichlorozirconium 7.50 g (33.2 mmol) of zirconium tetrachloride are added in portions over the course of 10 minutes to a suspension, cooled to −78° C., of 9.58 g (30.7 mmol) of the dilithium compound (Example 2) in 200 ml of toluene. After the mixture has been stirred at room temperature for 50 hours, the precipitate is filtered off via a frit, and the orange filtrate is evaporated to dryness in vacuo. Repeated washing with pentane gives 4.38 g of the zirconocene dichloride as an orange-yellow powder in a crude yield of 37%.

For purification, the orange-yellow powder is extracted for several days with pentane in a circulation frit, giving, after removal of the solvent in an oil-pump vacuum, 1.70 g (14%) of the zirconocene dichloride as a yellow powder: m.p. 223° C. (decomp., DSC).

EXAMPLE 11

Synthesis of 4-($\eta^5$-cyclopentadienyl)-4,7,7-trimethyl($\eta^5$-4,5,6,7-tetrahydroindenyl)dichlorotitanium A suspension of 5.46 g (17.5 mmol) of the dilithium etherate (Example 2) in 200 ml of toluene is cooled to −78° C., and 3.3 g (17.5 mmol) of titanium chloride are added. The reaction solution immediately becomes a dark red color. The mixture is stirred at room temperature for 30 hours, insoluble constituents are removed by filtration through a frit, and the dark-red toluene phase is evaporated to dryness in an oil-pump vacuum. Repeated washing with pentane gives 1.85 g of the titanocene dichloride as a brown-beige powder. The crude product is subsequently extracted for several days with pentane in a circulation frit, giving, after removal of the solvent, the titanocene dichloride as a brown solid in a yield of 13% (780 mg): m.p. 259° C. (decomp., DSC).

EXAMPLE 12

Synthesis of [4'-($\eta^5$-cyclopentadienyl)-4,7,7-trimethyl-($\eta^5$-4,5,6,7-tetrahydroindenyl)dichlorozirconium from 2,5-bis (2,4-cyclopentadien-1-ylidene) hexane 62.4 ml (99.8 mmol) of an ethereal 1.60M solution of methyllithium is slowly added at 0° C. with vigorous stirring to a solution of 10.0 g (47.5 mmol) of 2,5-bis (2,4-cyclopentadien-1-ylidene)hexane (Example 1) in 150 ml of toluene. When the addition is complete, the mixture is stirred at room temperature for 24 hours and then cooled to −30° C., and 9.32 g (40 mmol) of zirconium tetrachloride are added. After the mixture has been stirred at room temperature for 30 hours, LiCl is filtered off, and the filtrate is evaporated to dryness in vacuo. Repeated washing with pentane gives 4.02 g (26%) of the zirconium dichloride.

EXAMPLE 13

Synthesis of the two diastereomers of 4-($\eta^5$-cyclopentadienyl)-4,7-dimethyl-7-phenyl($\eta^5$-4,5,6,7-tetrahydroindenyl) dichlorozirconium 2.72 g (11.7 mmol) of zirconium tetrachloride are added in portions to a suspension cooled to −78 ° C., of 4.37 g (11.7 mmol) of the dilithium salt (Example 3) in 200 ml of toluene. The mixture is allowed to warm to room temperature, and the orange suspension is stirred at 20° C. for a further 20 hours. The mixture is filtered, the solvent is removed from the filtrate in an oil-pump vacuum, and the orange-red, oily residue is powdered by vigorous stirring in 20ml of pentane. Removal of the pentane in vacuum subsequently gives 2.64 g (50%) of the zirconocene dichloride as a yellow-orange powder. The $^1$H-NMR spectrum of the crude product suggests a diastereomer ratio of 8:1.

EXAMPLE 14

Synthesis of the two diastereomers of 4-($\eta^5$-cyclopantadienyl)-4,7-dimethyl-7-butyl(3-4,5,6,7-tetrahydroindenyl)dichlorozirconium A suspension of 7.80 g (22.0 mmol) of the dilithium salt (EXAMPLE 4) in 200 ml of toluene is cooled to −78° C., and 5.10 g (22.0 mmol) of zirconium tetrachloride are added in portions. The mixture is allowed to warm to room temperature, and the yellow-orange suspension is stirred for a further 48 hours. Insoluble constituents are filtered off via a frit, and the solvent is removed in an oil-pump vacuum. The red-orange oil is powdered by vigorous stirring with pentane, giving the zirconocene dichioride in a crude yield of 30% (2.72 g).

Purification is effected by extracting the crude product with pentane for several days in a circulation frit. The $^1$H-NMR spectrum of the fine, yellow precipitate indicates two sets of signals in a ratio of 15:1. A few crystals can be isolated from the yellow, concentrated filtrate by storage at −30° C. These crystals of the diastereomerically pure zirconocene dichloride (pR, 4R, 7R)-4-($\eta^5$-cyclo-pentadienyl)-4,7-dimethyl-7-butyl-($\eta^5$-4,5,6,7-tetrahydro-indenyl)dichlorozirconium) enable individual sets of signals in the $^1$H-NMR to be assigned. The crystals which have crystallized from the pentane solution correspond to the diastereomer formed in the lesser amount. Crystals can also be isolated from the 1.35 g (14%) of the yellow, fine powder by dissolving approximately 100 mg of powder in a little methylene chloride and allowing extremely slow crystallization by diffusion of pentane into this solution. The major product is the other diastereomer.

EXAMPLE 15

Synthesis of 4-($\eta^5$-cyclopentadienyl)-4,7-dimethyl-7-butyl($\eta^5$-4,5,6,7-tetrahydroindenyl)dichlorohafnium 1.81 g (5.6 mmol) of hafnium tetrachloride are added to a suspension, cooled to −78° C., of 2.00 g (5.64 mmol) of the dilithium salt (Example 4) in 150 ml of toluene. The orange suspension in allowed to warm to room temperature, and is stirred for a further 2 days in order to complete the reaction. Insoluble constituents are then filtered off via a frit, and the orange-red filtrate is evaporated to dryness on an oil pump 30 ml of pentane are added to the orange-red residue, and the mixture is stirred vigorously overnight. Removal of the solvent in vacuo gives the hafnocene dichloride as beige powder in a crude product yield of 700 mg (24%). The $^1$H-NMR spectrum of the crude product shows only one diastereomer.

EXAMPLE 16

Synthesis of the two diastereomers of 4-($\eta^5$-cyclopentadienyl)-4,7-dimethyl-7-butyl($\eta^5$-4,5,6,7-tetrahydroindenyl)dichlorotitantum Suspension of 5.95 g (16.8 mmol) of the dilithium salt (Example 4) in 120 ml of toluene and addition of 3.18 g of (16.8 mmol) of titanium tetrachoride at −78° C. causes the beige suspension immediately to change color to dark red. The suspension is stirred at room temperature for a further 36 hours, before the precipitate is separated off, and the dark red filtrate is evaporated to dryness in an oil-pump vacuum. The two diastereomers of the titanocene dichloride are obtained as a brown-red powder in a crude yield of 1.54 g (24%). The signals of the two diastereomers can be determined in the $^1$H-NMR spectrum of the crude product in a ratio of 8:1. Extraction of the brown-red powder with pentane for several days in a circulation frit causes a brown precipitate to form from the filtrate. The $^1$H-NMR spectrum shows that the pentane solution contains the two isomers in the ratio of 1:1 (150 mg, 2.3%) while the brown powder (720 mg, 11%) is virtually diastereomerically pure.

EXAMPLE 17

Synthesis of {4-[3'-t-Bu-($\eta^5$-cyclopentadienyl)]-4,7,7-trimethyl($\eta^5$-4,5,6,7-tetrahydroindenyl)}dichlorozirconium A suspension of 2.84 g (7.71 mmol) of the dilithium salt (Example 9) is suspended in 150 ml of toluene and cooled to −78° C. 1.79 g (7.71 mmol) of zirconium tetrachloride are added in portions, and the mixture is warmed to room temperature and stirred for a further 48 hours. Insoluble constituents are subsequently separated off, the orange toluene phase is evaporated in an oil-pump vacuum, and the orange-red oil is powdered by vigorous stirring in pentane. The regioismeric zirconocene dichlorides are obtained as an orange-yellow powder in a crude yield of 23% (787 mg). The $^1$H-NMR spectrum of the crude product show the signals of the two diastereomers in a ratio of 1:1. Extraction of the orange-yellow powder with pentane in a circulation frit gives 370 mg (11%) of the zirconocene dichlorides in a ratio of 1:1.

G. Synthesis of the dialkylmetallocane complexes

EXAMPLE 18

Synthesis of 4-($\eta^5$-cyclopentadienyl)-4,7,7-trimethyl($\eta^5$-4,5,6,7-tetrahydroindenyl)zirconiumdimethyl Following the literature procedure [b], 3.30 ml (5.33 mmol, 1.60M) of an ethereal solution of methyllithium are slowly added dropwise at −78° C. to a suspension of 1.03 g (2.66 mmol) of zirconocene dichloride (Example 10) in 50 ml of diethyl ether. The mixture is allowed to warm slowly to room temperature in a cold bath and is then stirred at room temperature for a further 5 hours. The solvent is removed in vacuo, and the colorless residue is extracted with 3×50 ml of pentane. The combined pentane solutions are evaporated and kept at −25° C. to crystallize. Removal of the solvent and drying in an oil-pump vacuum gives 700 mg (76%) of dimethylzirconocene as a colorless, crystalline powder.

[b] E. Samuel, M.D. Rausch, J.Am.Chm.Soc. 95 (1973) 6263.

EXAMPLE 19

Synthesis of the two diastereomers of [4-($\eta^5$-cyclopentadienyl)-4,7-dimethyl-7-(2-propen-1-yl) ($\eta^5$-4,5,6,7-tetrahydroindenyl)]dichlorotitanium 2.45 g (7.24 mmol) of the dilithium compound (Example 9b) are dissolved in 80 ml of tetrahydrofuran, giving an orange, clear solution, which is subsequently cooled to −78° C., and 2.42 g (7.24 mmol) of titanium tetrachloride/bis-THF adduct are added. The reaction mixture immdiately changes color to dark red. The mixture is allowed to warm to room temperature and is stirred for a further two days. Removal of the solvent in vacuo gives a brown powder. Pentane extraction of the crude product in a circulation frit give 0.22 g (9%) of the two allyltitanocenes as a brown powder.

The $^1$H-NMR spectrum shows the two products in a diastereomer ratio of 2:1.

EXAMPLE 20

Synthesis of the two diastereomers of [4-($\eta^5$-cyclopentadienyl)-4,7-dimethyl-7-(2-propen-1-yl) ($\eta^5$-4,5,6,7-tetrahydroindenyl)]dichlorozirconium 7.56 g (22.3 mmol) of the dilithium compound (Example 9b) are suspended in 200 ml of toluene and cooled to −78° C. 5.21 g (22.3 mmol) of zirconium tetrachloride are added in portions. After 30 minutes at −78° C. the mixture is allowed to warm to room temperature over the course of 4 hours and is stirred for a further 12 hours. The orange suspension is then filtered through a G4 frit the residue is washed twice with 30 ml of toluene in each case, and the filtrate is evaporated to dryness in an oil-pump vacuum, giving an orange oil, which can be powderd by addition of 50 ml of pentane followed by vigorous stirring. Removal of the solvent in vacuo gives the yellow-orange, pulverulent allylzirconocenes in a crude yield of 5.04 g (55%). Repeated extraction of the crude product with 100 ml of pentane in a circulation frit gives 2.34 g (21%) of the allylzirconocenes as a yellow powder m.p. 99° C. (DSC).

The $^1$H-NMR spectrum shows the two products 23a and 23b in a diastereomer rato of 1.5:1.

EXAMPLE 21

Synthesis of the two diastereomers of [4-($\eta^5$-cyclopentadienyl)-4,7-dimethyl-7-(3-(9-borabicyclono{3,3,1}nonyl-β) propyl-($\eta^5$-4,5,6,7-tetrahydroindenyl)]dichlorozirconium 210 mg (0.51 mmol) of the allylzirconocene dichlorides (Example 20) are dissolved in 50 ml of toluene, and 62 mg (0.51 mmol) of 9 BBN are added at room temperature. The mixture is stirred at room temperature for 36 hours, the solvent is removed in vacuo, and the orange-yellow oil is powdered using 30 ml of diethyl ether. Evaporation of the clear soluton to 10 ml and cooling for several hours at −30° C. gives 208 mg (78%) of the diastereomers as an orange-yellow powder; m.p. 74° C. (DSC).

EXAMPLE 22

Synthesis of 7-(3'-i-propylcyclopentadienyl)-4,4,7-trimethyl-4,5,6,7-tetrahydro-1H-indene a) Synthesis of {4-[3'-i-propyl-($\eta^5$-cyclopentadienyl)]-4,7,7-trimethyl($\eta^5$-4,5,6,7-tetrahydroindenyl)}dichlorozirconium A solution of 6.11 g (22.9 mol) of the tetrahydroindenyl-fulvene indenylfulvene (Example 8a) in 20 ml of diethyl ether is added dropwise at room temperature to a suspension of 2.17 g (57.3 mmol) of lithium aluminum hydride in 100 ml of diethyl ether. After a vigorous, but not very exothermic reaction, the orange suspension in refluxed for a further three hours, cooled to 0° C. in an icebath and carefully hydrolyzed by means of ice-water, giving a white, bulky precipitate, which in extracted twice with 50 ml of diethyl ether in each case, and the combined organic phases are washed with aqueous sodium chloride solution. Drying over magnesium sulfate and removal of the solvent in vacuo give 5.63 g (92%) of the i-propylsubstituted ansa-ligand as an orange oil.

The product again comprises a plurality of double-bond isomers, so that only a rough assignment of signal groups in the $^1$H-NMR spectrum is possible.

b) Synthesis of {4-[3'-i-propyl-($\eta^5$-cyclopentadienyl)]-4,7,7-trimethyl($\eta^5$-4,5,6,7-tetrahydroindenyl)}dilithium 4.21 g (15.7 mmol) of the isopropyl-substituted ligand are dissolved in 70 ml of diethyl ether, and 21.6 ml (34.5 mmol) of a 1.60M solution of methyllithium are added dropwise at 0° C. The solution rapidly becomes colorless, and a white precipitate forms. When the dropwise addition is complete the mixture is stirred at room temperature for a further 15 hours. The precipitate in then filtered off and washed twice with 15 ml of diethyl ether in each case, giving 5.20 g (93%) of the extremely air-sensitive dilithium salt as a beige powder containing one mole-equivalent of diethyl ether.

a) Synthesis of {4-[3'-i-propyl($\eta^5$-cyclopentadienyl)]-4,7,7-trimethyl($\eta^5$-4,5,6,7-tetrahydroindenyl)}dichlorozirconium 3.40 g (14.6 mmol) of zirconium tetrachloride are slowly added to a suspension, cooled to −78° C., of 5.30 g (14.7 mmol) of the dilithium salt in 200 ml of toluene. The resultant beige suspension is stirred at room temperature for 24 hours, before insoluble constituents are separated off and the orange, clear filtrate is evaporated to approximately 50 ml in an oil-pump vacuum. $^1$H-NMR spectroscopic analysis of the toluene phase shows that the two diastereomers are present therein in a ratio of 1:1. Addition of 20 ml of pentane and storage in the ice box at −20° C. causes precipitation of a yellow solid (1.42 g) in which one diastereomer is significantly concentrated (8:1). Accordingly, the toluene phase contains the other diastereomer concentrated in the reverse ratio (1:62 g); overall yield 49%.

Dissolution of approximately 100 mg of the precipitated yellow powder in methylene chloride and slow diffusion of pentane into this solution gives crystals suitable for X-ray structure analysis, which shows that they are the diastereomer {4R*-{4-[3'-i-Pr-($\eta^5$-cyclopentadienyl)]- 4,7,7-trimethyl($\eta^5$-4,5,6,7-pR*-tetrahydroindenyl)}-dichlorozirconium.

EXAMPLE 23

Synthesis of
{4-[3'-i-Propyl($\eta^5$-cyclopentadienyl)-4,7,7-trimethyl[2-i-propyl($\eta^5$-4,5,6,7-tetrahydroindenyl)}-dichlorozirconium a) Synthesis of 4-(3'-i-propylcyclopentadienyl)-4,7,7-trimethyl-(2-i-propyl-4,5,6,7-tetrahydro-1H-indene) starting from 2-isopropylidene-4-(3'-isopropylidenecyclopenta-1',4'-dienyl)-4,7,7,-trimethyl-(4,5,6,7-tetrahydro-2H-indene)

Dissolution of 8.32 g (34.2 mmol) of the "monofulvene" (Example 8a) in a mixture of 50 ml of methanol and 20 ml of pentane gives an orange-red, clear solution, which is cooled a 0° C. Successive addition of 2.61 g (3.31 ml, 45.0 mmol) of acetone and 6.08 g (7.10 ml 85.5 mmol) of pyrrolidine causes the reaction solution to change color to dark red after 30 minutes. The reaction mixture is stirred at room temperature for 7 days, and 5 ml of glacial acetic acid, 150 ml of water and 50 ml of pentane are added sucuessively. The aqueous phase is extracted by shaking twice with pentane, and the combined organic phases are washed several times with saturated, aqueous sodium chloride solution and dried over magnesium sulfate. Removal of the solvent in an oil-pump vacuum gives the difulvene as a red oil in a crude yield of 9.04 g (86%).

Some of the red oil is taken up in pentane and chromatographed on a silica gel column (Merck, 60 mesh) which has previously been deactivated by means of triethylamine. The eluent used is a pentane:diethyl ether mixture (100:5) (overall yield<10%).

b) synthesis of 4-(3'-i-propylcyclopentadienyl)-4,7,7-trimethyl(2-i-propyl-4,5,6,7-tetrahydro-1H-indene)

3.03 g (80.0 mmol) of lithium aluminum hydride in 100 ml of diethyl ether are introduced into a three-neck flask fitted with coil condenser and dropping funnel, and 6.47 g (21.1 mmol) of the difulvene (Example 23a) dissolved in 50 ml of diethyl ether are added dropwise at room temperature with vigorous stirring. When the addition is complete, the reaction mixture is refluxed for a further 5 hours and then carefully hydrolyzed using 100 ml of water, giving a gray precipitate of aluminum oxide and a yellow diethyl ether phase. The latter is decanted off, the gray precipitate is extracted a number of times with diethyl ether, and the combined diethyl ether phases are washed with saturated, aqueous sodium chloride solution. Drying over magnesium sulfate and removal of the solvent in vacuo give 6.25 g (96%) of the reduced difulvene as an orange-red oil, which is reacted without further purification.

c) synthesis of 4-(3'-i-propylcyclopentadienyl)-4,7,7-trimethyl(3-i-propyl-4,5,6,7-tetrahydro-1H-indene) via 2,5-bis [(i-propyl)cyclopenta-2,4-dien-1-ylidene]hexane 5.90 ml (5.07 g, 71.3 mmol) of freshly distilled pyrrolidine are added dropwise at 0° C. to a solution of 2.78 ml (2.71 g. 23.8 mmol) of 2,5-hexanedione and 4.00 g (47.6 mmol) of isopropylcyclopentadiene in 50 ml of methanol. During this addition, the reaction solution immediately changes color to dark red and is stirred at 0° C. for a further 15 hours. For work-up. the pyrrolidine is neutralized by addition of a solution of 2 ml of glacial acetic acid in 100 ml of water. The mixture is extracted twice with 100 ml of diethyl ether in each case, the combined organic phases are washed several times with saturated, aqueous sodium chloride solution and dried over magnesium sulfate. Removal of the solvent in vacuo gives the difulvene as a dark-red oil in a crude yield of 75% (5.20 g)

The difulvene is purified by column chromatography in a silica gel column, deactivated by means of triethylamine (pentaneitriethylamine=100:1). A suitable eluent is a pentane:diethyl ether solvent mixture in a ratio of 1:1, allowing the isolation of 1.72 g of the difulvene (25%) as a red oil.

d) Synthesis of 4-(3'-i-propylcyclopentadienyl)-4,7,7- trimethyl(2-i-propyl-4,5,6,7-tetrahydro-1H-indene)

600 mg (2.04 mmol) of the bisisopropyl-substituted difulvene (Exauple 23b) are dissolved in 10 ml of diethyl ether, and 2.55 ml of an ethereal 1.60M solution of methyllithium are slowly added at 0° C. The mixture is allowed to warm to room temperature, giving, after 24 hours, an orange suspension, which is cooled to 0° C. before it is hydrolyzed by means of 10 ml of water. Extraction with 20 ml of diethyl ether and drying over magnesinum sulfate gives 520 mg of the cyclized product as an orange oil in a yield of 82%.

e) Synthesis of {4-[3'-i-propyl($\eta^5$-cyclopentadienyl)]-4,7,7-trimethyl[2-i-propyl($\eta^5$-4,5,6,7-tetrahydroindinyl)}dichlorozirconium 2.00 ml (3.22 mmol) of a 1.60 M ethereal solution of methyllithium are added dropwise at 0° C. to a solution of 500 mg (1.61 mmol) of the bisisopropyl-substituted compounds (Example 23a and 23b) in 20 ml of pentane. The mixture is allowed to warm to room temperature, giving, after 12 hours, a cloudy, orange suspension, which is cooled to −78° C. and treated with 373 mg (1.61 mmol) of zirconium tetrachloride. After the mixture has been stirred at room temperature for 24 hours, the insoluble constituents are filtered off, and the solvent is removed in vacuo, giving the two diastereomers of the ansazirconocene as an orange powder in a crude yield of 300 mg (40%). The $^1$H-NMR spectrum shows the resonance signals of the two diastereomers in the ratio 1:1 (determined from the i-Pr groups).

EXAMPLE 24

Synthesis of {4-[3'-trimethylsilyl
($\eta^5$-cyclopentadienyl)]-4,7,7-trimethyl[2-trimethylsilyl($\eta^5$-4,5,6,7-tetrahydroindenyl)]}dichlorozirconium a) synthesis or 7-(3'-trimethylsilylcyclopentadienyl)-4,4,7-trimethyl(2-trimethylsilyl-4,5,6,7-tetrahydro-1H-indene)

A solution of 6.81 g (21.8 mmol) of the dilithium etherate (Example 2) in 50 ml of tetrahydrofuran is cooled to 0° C., and 5.50 ml (4.74 g, 43.6 mmol) of trimethylsilyl chloride are added dropwise. The mixture is allowed to warm to room temperature overnight, giving an orange, cloudy suspension, which is hydrolyzed by addition of 50 ml of degassed water and subsequently extracted with petroleum ether. Drying over magnesium sulfate and removal of the solvent in vacuo gives 6.14 g (81%) of a red-orange oil.

b) Synthesis of {4-[3'-trimesthylsilyl($\eta^5$-cyclopentadienyl}]4,7,7-trimethyl[2-trimethylsilyl($\eta^5$-4,5,6,7-tetrahydroindenyl)]}dilithium 11.1 ml (17.8 mmol) of a 1.80M ethereal solution of methyllithium are added dropwise to a solution, cooled to 0° C., of 3.30 g (8.90 mmol) of the bistrimethylsilyl-substituted compound in 40 ml of pentane. A white precipitate is obtained and gas is evolved. The mixture is stirred at room temperature for a further 24 hours in order to complete the reaction, before the white precipitate is filtered off and washed with pentane. Drying in an oil-pump vacuum give the dilithium salt as a white, pyrophoric residue in a yield of 76% (2.60 g).

c) synthesis of {4-[3'-trimethylsilyl($\eta^5$-cyclopentadienyl)]-4,7,7-trimethyl[2-trimethylsilyl($\eta^5$-4,5,6,7-tetrahydroindenyl)]}dichlorozirconium 1.58 g (6.79 mmol) of zirconium tetrachloride are added in portions to a suspension cooled to −78° C., of 2.60 g (6.79 mmol) of the bistrimethylsilyl-substituted dilithium salt in 100 ml of toluene. The mixture is allowed to warm to room temperature, giving, after stirring for 24 hours, an orange suspension. Insoluble constituents are separated off, and the solvent is evaporated to dryness, giving a red oil. Addition of 20 ml of pentane followed by work-up gives the two diastereomers of the ansa-ziraconocene as an orange powder in a crude yield of 1.54 g (43%), m.p. 151° C. (decomp., DSC).

II. Polymerization examples

Examples A–M

General Experimental Procedure

The cocatalyst methylaluminoxane is introduced into a 500 ml polymerization reactor, dissolved in 250 ml of toluene and cooled to −50° C. Propene is passed through the solution by means of a gas inlet tube and thus condensed in, excess propene being able to escape through a bubble counter. As soon as the desired amount of liquid propene in present (about 30 to 35 ml), the inlet tube is closed. The desired polymerization temperature is then established. After conditioning, a solution of the catalyst in a little toluene is added. After an appropriate reaction time, the reaction is terminated by addition of 500 ml of methanol in hydrochloric acid, the excess propene escaping as the solution boils vigorously. The polymers are isolated by separating off the toluene phase and extracting the water/methanol phase with diethyl ether. The combined toluene and diethyl ether phasea are then evaporated to dryness in vacuo.

The experimental results achieved are shown in the table below:

Propene polymerization using ansa-metallocene/methyl-aluminoxane catalyst systems, where the metallocenes employed were 4-($\eta^5$-cyclopentadienyl)-4,7,7-trimethyl($\eta^5$-4,5,6,7-tetrahydroindenyl)dichlorotitanium (a), 4($\eta^5$-cyclopentadienyl)-4,7,7-trimethyl($\eta^5$-4,5,6,7-tetrahydroindenyl)dichlorozirconium (b) and 4-($\eta^5$-cyclopentadienyl)- 4,7-dimethyl-7-phenyl($\eta^5$-4,5,6,7-tetrahydroindenyl)dichlorozirconium (c).

In all cases, the cocatalyst employed was a 10.6% strength by weight solution of methyl aluminoxane in toluene. The activities arm calculated from the following equation:

Activity=$gPP/g[M]\cdot t\cdot p$)

where
gPP=amount of polypropylene in g
g[M]=amount of transition metal in the catalyst
t=duration in h
p=pressure in bar Example N a) Preparation of the Catalyst Component

[4-($\eta^5$-cyclopentadienyl)-4,7,7-trimethyl($\eta^5$-4,5,6,7-tetrahydroindenyl)dichlorozirconium was supported on $SiO_2$ as EP 567 952.

b) Gas-Phase Polymerization of Ethylene

Ethylene was polymerized in the gas phase in a 2 $dm^3$ steel autoclave with polished walls. The fluidized bed was generated mechanically with the aid of a double-helix stirrer shaped to match the autoclave wall, with initial introduction of 10 g of polyethylene powder as seed bed. First the cocatalyst (2 mmol of triisobutylaluminum in 2 $cm^3$ of isopentane) and then 1 g of the catalyst mixture (25.8 μmol at Zr) were metered in via a pressure buret. The polymerization was subsequently carried out for 1 hour at a temperature of 80° C. and an ethylene partial pressure of 8 bar and terminated by releasing the pressure in the autoclave.

36 g of polyethyleme having a VN of 70 ml/g were obtained, corresponding to an activity of 3.6 kg of PE/g metallocene.

Examples O–T

A dry 1.5 $dm^3$ reactor was flushed with nitrogen and filled at 20° C. with 0.75 $dm^3$ of a gasoline fraction having the boiling range of 100° to 120° C. from which the aromatic components had been removed. The gas space of the reactor was then flushed free of nitrogen by injecting 2 bar of propylene and releasing the pressure and repeating this operation four times. 3.75 $dm^3$ of a toluene solution of methylaluminoxane (5 mmol of Al, n=18) were then added. The reactor was heated to 30° C. with stirring and, at a stirring speed of 500 rpm, the preparation of the reactor was completed by addition of the monomers (partial pressure of ethylene and propylene and the amount of 5-ethylidene-2-norbornene (in $cm^3$) see table)

| Example | Metallocane | T [°C.] | Time [min] | Cat. [mg] | Cocat./cat. ratio | PP [g] | Activity | Mη |
|---------|-------------|---------|------------|-----------|-------------------|--------|----------|--------|
| A | a) | −60 | 300 | 20 | 550 | 2.3 | 110 | — |
| B | a) | −50 | 240 | 20 | 550 | 4.7 | 300 | 680000 |
| C | a) | −40 | 240 | 20 | 550 | 5.8 | 370 | 290000 |
| D | a) | −30 | 240 | 19 | 590 | 8.7 | 650 | 210000 |
| E | a) | −20 | 180 | 20 | 550 | 5.6 | 500 | 56000 |
| F | a) | −11 | 180 | 19 | 590 | 12.5 | 1100 | 23000 |
| G | a) | 0 | 120 | 22 | 500 | 11.2 | 1300 | 9000 |
| H | b) | −50 | 300 | 20 | 320 | 0.4 | 16 | 28000 |
| I | b) | −30 | 240 | 20 | 320 | 6.3 | 330 | 25000 |
| J | b) | −5 | 240 | 20 | 320 | 29.5 | 1500 | 2100 |
| K | b) | 22 | 120 | 20 | 620 | 16.8 | >2200 | — |
| L | b) | 70 | 60 | 10.6 | 2200 | 1000 | 13300 | — |
| M | c) | −30 | 240 | 19 | 390 | 2.8 | 180 | — |

In parallel, 0.125 mg of the metallocene 4-($\eta^5$-3'-methyl-cyclopentadienyl)-4,7,7-trimethyl($\eta^5$-2-methyl-4,5,6,7-tetrahydroindenyl)dichlorozirconium were dissolved in 1.25 cm$^3$ of a toluene solution of the methylaluminoxane (1.67 mmol of Al, n=18) and reacted completely by standing for 15 minutes. The solution was then introduced into the reactor, and the polymerization system was warmed to 50° C. and kept at this temperature for 1 hour by appropriate cooling. The polymerization was the terminated by addition of 2 ml of isopropanol, and the polymer was precipitated by discharging the reactor contents into acetone and dried at 80° C. in vacuo (stabilized with Irganox 1010, 0.1% by weight). The polymerization results are likewise shown in the table.

oughly with ethene. The solution was saturated with ethene by repeatedly injecting ethene (1 bar). 10 cm$^3$ of a toluene solution of methylaluminoxane (10.1% strength by weight of methylaluminoxane solution having a molecular weight of 1300 g/mol according to cryoscopic determination) were metered in countercurrent into the reactor prepared in this way. A solution of 10 mg of 4-$\eta^5$-isopropylcyclopentadienyl-4,7,7-trimethyl($\eta^5$-4,5,6,7-tetrahydroindenyl)dichlorozirconium in 10 cm$^3$ of a toluene solution of methylaluminoxane were added after preactivation for 15 minutes. (In the case of molecular weight regulation using hydrogen, hydrogen can be injected at this point).

TABLE

| | | | Copolymers and terpolymers | | | | | |
|---|---|---|---|---|---|---|---|---|
| | | | Amount of 5-ethylidene- | Yield [kg of | | | Comonomer content | |
| Example | Partial pressure of propylene | Partial pressure of ethylene | 2-norbornene [ENB] [cm$^3$] | polymer/g of metal × h] | VN [cm$^3$/g] | Tg [°C.] | Ethylene [% by weight] | ENB [% by weight] |
| O | 2.5 | 0.5 | — | 14 | 26 | −15.5 | 5.3 | — |
| P | 1.0 | 3.0 | — | 12 | 41 | −55.9 | 35.0 | — |
| Q | 1.0 | 3.0 | 1.25 | 20 | 50 | −55.1 | 40.8 | 2.5 |
| R | 1.0 | 3.0 | 2.5 | 24 | 51 | −56.3 | 44.2 | 4.3 |
| S | 1.0 | 3.0 | 5.0 | 15 | 52 | −46.5 | 48.1 | 9.4 |
| T | 1.0 | 3.0 | 10.0 | 26 | 50 | −51.9 | 49.4 | 12.2 |

Example U 600 cm$^3$ of a solution of 180 cm$^3$ of styrene (distilled under reduced pressure) in toluene were introduced into a 1.5 dm$^3$ autoclave which had previously been flushed thoroughly with argon. The solution was saturated with argon by repeatedly injecting argon (1 bar). 10 cm$^3$ of a toluene solution of methylaluminoxane (10.1% strength by weight of methylaluminoxane solution having a molecular weight of 1300 g/mol according to cryoscopic determination) were metered in countercurrent into the reactor prepared in this way. A solution of 10 mg of 4-($\eta^5$-isopropylcyclopentadienyl-4,7,7-trimethyl($\eta^5$-4,5,6,7-tetrahydroindenyl)dichlorozirconium in 10 cm$^3$ of a toluene solution of methylaluminoxane were added after preactivation for 15 minutes. (In the case of molecular weight regulation using hydrogen, hydrogen can be injected at this point).

The mixture was polymerized for two hours with stirring (750 rpm), during which the temperature in the reactor was kept at 70° C.

When the reaction time was complete, the polymerization mixture was discharged into a vessel and immediately introduced into 5 dm$^3$ ethanol, the mixture was stirred for 10 minutes, and the precipitated product was subsequently filtered. The filter cake was washed alternately, three times each with 10% strength hydrochloric acid and ethanol and subsequently washed with water until neutral, and the residue was slurried in ethanol and refiltered. The polymer purified in this way was dried in vacuo (0.2 bar) at 80° C. for 15 hours.

Drying gave 5.2 g of polymer having a glass transition tensperature of 102° C.

Example Ul 600 cm$^3$ of a solution of 180 cm$^3$ of styrene (distilled under reduced pressure) in toluene were introduced into a 1.5 dm$^3$ autoclave which had previously been flushed thor- The mixture was polymerized for one hour with stirring (750 rpm). and the ethene pressure was kept at 1 bar by subsequent metering in and the temperature in the reactor was kept at 70° C.

When the reaction times was complete, the polymerization mixture was discharged into a vessel and immediately introduced into 5 dm$^3$ of ethanol, the mixture was stirred for 10 minutes, and the precipitated product was subsequently filtered. The filter cake was washed alternately, three times each, with 10% strength hydrochloric acid and ethanol and subsequently washed with water until neutral, and the residue was slurried in ethanol and refiltered. The polymer purified in this way was dried in vacuo (0.2 bar) at 80° C. for 15 hour.

Drying gave 21 g of colorless polymer having a glass transition temperature of −24° C. and a viscosity number of 30 cm$^3$/g.

EXAMPLE V

In order to prepare the catalyst solution, 10 mg of metallocene A are dissolved in 10 ml of MAO solution in toluene, and the mixture in stirred for 15 minutes. In parallel a 1.5 dm$^3$ stirred reactor which has been rendered inert in filled with 900 ml of diesel oil (boiling poInt 100° to 120° C.) and conditioned at 70° C. The catalyst solution is metered in, and the mixture is polymerized for 1 hour at 750 rpm by means of 7 bar of ethylene. The presuure in the reactor is then released, and the polymer is filtered off from the suspension, washed with acetone and dried for 12 hours in a vacuum drying cabinet, giving 39.2 g of polyethylene having a VN or 72 ml/g.

Examples W to EA

Example A was repeated using the stated amounts of metallocenes 1 to 5, the polymerization temperature being 50° and 85° C. in examples BA and DA respectively, and 0.5 bar of hydrogen made up into 7 bar with ethylene being used in Examples X and EA.

1: [4-($\eta^5$-cyclopentadienyl)-4,7,7-trimethyl($\eta^5$-4,5,6,7-tetrahydroindenyl)]dichlorozirconium 2: [4-($\eta^5$-cyclopentadienyl)4,7-dimethyl-7-butyl($\eta^5$-4,5,6,7-tetrahydroindenyl)]dichlorozirconium 3: [4-($\eta^5$-cyclopentadienyl)-4,7-dimethyl-7-phenyl($\eta^5$-4,5,6,7-tetrahydroindenyl)]dichlorozirconium 4: [4-($\eta^5$-3-methylcyclopentadienyl)-4,7,7-dimethyl($\eta^5$-4,5,6,7-tetrahydroindenyl)]dichlorozirconium 5: [4-($\eta^5$-3-tert-butylcyclopentadienyl)-4,7,7-dimethyl($\eta^5$-4,5,5,7-tetrahydroindenyl)]dichlorozirconium

| Ex. | Met | [mg] | Temperature [°C.] | Ethylene [bar] | $H_2$ [bar] | Activity [kg/g of metallocene/h] | VN [mg/g] |
|---|---|---|---|---|---|---|---|
| W  | 1 | 10 | 70 | 7   | 0   | 3.92 | 72  |
| X  | 1 | 10 | 70 | 6.5 | 0.5 | 3.8  | 20  |
| Y  | 2 | 10 | 70 | 7   | 0   | 11.8 | 100 |
| Z  | 3 | 7  | 70 | 7   | 0   | 2    | 75  |
| AA | 4 | 2  | 70 | 7   | 0   | 37   | 186 |
| BA | 5 | 8  | 50 | 7   | 0   | 4.2  | 320 |
| CA | 5 | 8  | 70 | 7   | 0   | 39   | 205 |
| DA | 5 | 4  | 85 | 7   | 0   | 68.4 | 70  |
| EA | 5 | 8  | 70 | 6.5 | 0.5 | 24.8 | 44  |

Example FA 500 ml of diesel oil (Bp. 100° to 120° C.), 20 ml of hexene and 10 ml of a 10% strength by weight solution of methylaluminoxane in toluene were introduced into a laboratory autoclave under nitrogen and conditioned to 70° C. with stirring at 700 rpm. In parallel, 10 mg of metallocene 5 were dissolved in 1 ml of 10% strength by weight MAO solution in toluene.

The polymerization was initiated by addition of the metallocene/MAO solution and by injection of 4 bar of ethylene. After 15 minutes, the polymerization was terminated using $CO_2$, and the reactor contents were discharged into 200 ml of methanolic HCl. The mixture was stirred for 5 hours in order to remove aluminum, and the polymer was subsequently filtered off and washed with water and acetone and dried at 80° C. for 12 hours in vacuo in order to determine the yield.

4.8 g of ethylene-1-hexene copolymer having a VN of 70 mg/g were obtained. In order to remove residual comonomer, a 1 g sample was dissolved in hot diesel oil (Bp. 100° to 120° C.), precipitated, filtered off, washed with acetone and re-dried at 80° C. in vacuo. The DSC showed a melting point of 110.5° C., and the $^{13}$C-NMR showed a hexene content of 4.6 mmol %.

Example GA

Example J was repeated using 10 mg of metallocene 6 ([4-($\eta^5$-3-isopropylcyclopentadienyl)-4,7,7-diethyl-($\eta^5$-4,5,6,7-tetrahydroindenyl)]dichlorozirconium), giving 4 g of copolymer having a VN of 22 mg/g which, after purification, had a DSC melting paint of 102° C. and, according to $^{13}$C-NMR, a hexene content of 7.1 mol %.

We claim:

1. A process for the preparation of a polyolefin by polymerization of at least one olefin in the presence of at least one stereorigid metallocene compound containing, as ligands, at least two substituted or unsubstituted cyclopentadienyl groups bonded to one another via a monocyclic ring system, in which at least one cyclopentadienyl group is fused to the monocyclic ring system and one cyclopentadienyl group is a substituent on the monocyclic ring system.

2. The process as claimed in claim 1, in which the stereorigid metallocene compound has a ligand system other than 4-($\eta^5$-3-alkylcyclopentadienyl)-4,6,6-trimethyl($\eta^5$-2-alkyl-4,5-tetrahydropentalene).

3. The process as claimed in claim 1, in which the monocyclic or polycyclic ring system of the stereorigid metallocene compound has at least six ring atoms.

4. The process as claimed in claim 1, where the stereorigid metallocene compound has the formula I

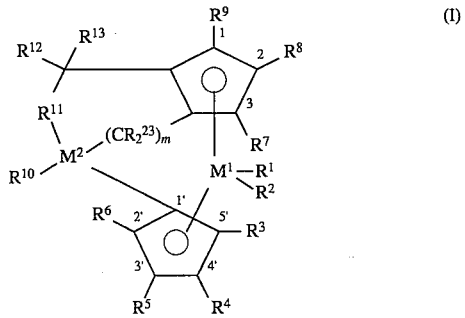

in which $M^1$ is a metal from group IIIb, IVb, Vb or VIb of the Periodic Table, $M^2$ is carbon, silicon, or germanium, $R^1$ and $R^2$ are identical or different and are a hydrogen atom, a $C_1$–$C_{40}$-hydrocarbon-containing group, an OH group, a halogen atom or in which $R^{14}$ is a halogen atom, a $C_1$–$C_{10}$-alkyl group or a $C_6$–$C_{10}$-aryl group, or $R^1$ and $R^2$ together with the atoms connecting them, from a ring system, $R^3$, $R^4$, $R^5$, $R^6$, $R^7$, $R^8$ and $R^9$ are identical or different and are a hydrogen atom, a halogen atom, a $C_1$–$C_{20}$-hydrocarbon containing group, a —Si$R^{14}_3$, —N$R^{14}_2$, —SiO$R^{14}_3$, —SiS$R^{14}_3$, or —P$R^{14}_2$, radical, in which $R^{14}$ is a halogen atom, a $C_1$–$C_{10}$-alkyl group or a $C_6$–$C_{10}$-aryl group, or two or more adjacent radicals $R^3$, $R^4$, $R^5$, $R^6$, $R^7$, $R^8$ and $R^9$, together with the atoms connecting them, form a ring system, $R^{10}$ is a hydrogen atom or a $C_1$–$C_{40}$-hydrocarbon-containing group, which may carry —N$R^{14}_3$, —Si$R^{14}_3$, —S$R^{14}_3$ or —OSi$R^{14}_3$ radicals, in which $R^{14}$ is a halogen atom, a $C_1$–$C_{10}$-alkyl group or a $C_6$–$C_{10}$-aryl group, or $R^{10}$ is connected to one or more of the radicals $R^3$, $R^4$, $R^5$ and $R^6$, $R^{11}$ is

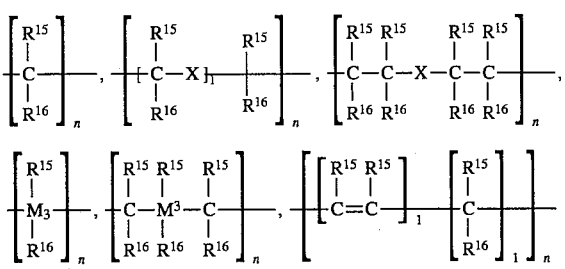

-continued

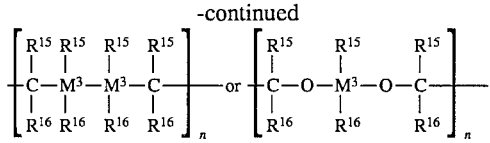

where
n is an integer from 1 to 20,
l is an integer from 0 to 20,
X is O, $=NR^{14}$, $=CO$, $PR^{14}$, $=P(O)R^{14}$, $=SO$, $=SO_2$, or —S—, in which $R^{14}$ is a halogen atom, a $C_1$–$C_{10}$-alkyl group or a $C_6$–$C_{10}$-aryl group,
$R^{15}$ and $R^{16}$ are identical or different and are a hydrogen atom, a halogen atom, or a $C_1$–$C_{40}$-hydrocarbon containing group, or two radicals $R^{15}$, two radicals $R^{16}$ or $R^{15}$ and $R^{16}$, in each case together with the atoms connecting them, form one or more rings, and $M^3$ is silicon, germanium, or tin,
$R^{12}$ and $R^{13}$ are identical or different and are a hydrogen atom, a $C_1$–$C_{40}$-hydrocarbon-containing group, which may carry —$NR^{14}{}_3$, —$SR^{14}{}_2$, —$SiR^{14}{}_3$ or —$OSiR^{14}{}_3$ radicals, in which $R^{14}$ is a halogen atom, a $C_1$–$C_{10}$-alkyl group, or a $C_6$–$C_{10}$-aryl group, or may carry halogen,
$R^{23}$ is identical or different and is a hydrogen atom, a halogen atom, or a $C_1$–$C_{40}$-hydrocarbon-containing group, or one or more radicals $R^{23}$ are bonded to one or both radicals $R^{15}$ and $R^{16}$ and/or to one or more radicals $R^{10}$, $R^{11}$, $R^{12}$ and $R^{13}$, and
m is an integer from 0 to 24.

5. The process as claimed in claim 4, in which $M^1$ is zirconium, $R^1$ and $R^3$ are identical and are a halogen atom, $R^3$, $R^4$, $R^5$, $R^6$, $R^7$, $R^8$ and $R^9$ are identical or different and are hydrogen or a $C_1$–$C_4$-alkyl group or a $C_6$–$C_{14}$-aryl group, or $R^8$ and $R^9$ and $R^3$ and $R_4$ and/or $R^5$ and $R^6$, together with the atoms connecting them, form an aromatic hydrocarbon ring system, $M^2$ is a carbon atom, $R^{10}$ is a $CH_1$–$CH_6$-alkyl group, $R^{11}$ is —$C_2$—$C_2$—, $R^{12}$ and $R^{13}$ are identical or different and are a methyl or phenyl group, and m=0.

6. The process as claimed in claim 1, wherein the process is conducted in the presence of at least one cocatalyst.

7. The process as claimed in claim 6, in which the cocatalyst is an aluminoxane.

8. The process as claimed in claim 1,
in which the stereorigid metallocene compound is supported and/or prepolymerized.

9. The process as claimed in claim 1,
in which one or more olefins of formula $R^a$—CH=CH—$R^b$ are polymerized, in which $R^a$ and $R^b$ are identical or different and are a hydrogen atom or a hydrocarbon radical having 1 to 20 carbon atoms, or $R^a$ and $R^b$, together with the atoms connecting them, form one or more rings.

10. A process for the preparation of a polyolefin by polymerization of at least one olefin in the presence of at least one stereorigid metallocene compound containing, as ligands, at least two substituted or unsubstituted cyclopentadienyl groups bonded to one another via a polycyclic ring system, in which at least one cyclopentadienyl group is fused to the polycyclic ring system.

* * * * *